US006989364B1

(12) United States Patent
Jin et al.

(10) Patent No.: US 6,989,364 B1
(45) Date of Patent: Jan. 24, 2006

(54) METHODS FOR TREATING CARDIAC HYPERTROPHY BY ADMINISTERING IFN-γ

(75) Inventors: Hongkui Jin, San Bruno, CA (US); Hsienwie Lu, Needham, MA (US); Nicholas F. Paoni, Belmont, CA (US); Renhui Yang, San Bruno, CA (US)

(73) Assignee: Genentech, Inc., South San Francisco, CA (US)

( * ) Notice: Subject to any disclaimer, the term of this patent is extended or adjusted under 35 U.S.C. 154(b) by 340 days.

(21) Appl. No.: 09/715,739

(22) Filed: Nov. 16, 2000

Related U.S. Application Data

(63) Continuation of application No. 09/273,099, filed on Mar. 19, 1999, now Pat. No. 6,187,304.

(60) Provisional application No. 60/080,448, filed on Apr. 2, 1998.

(51) Int. Cl.
*A01N 37/18* (2006.01)
*A61K 38/00* (2006.01)
*A61K 38/21* (2006.01)
*C07K 1/00* (2006.01)
*C07K 14/00* (2006.01)

(52) U.S. Cl. .......................... 514/2; 530/350; 424/85.4; 424/85.5

(58) Field of Classification Search .................... 514/2; 530/350; 424/85.4, 85.5
See application file for complete search history.

(56) References Cited

U.S. PATENT DOCUMENTS

| | | | |
|---|---|---|---|
| 4,727,138 A | 2/1988 | Goeddel et al. | |
| 4,762,791 A | 8/1988 | Goeddel et al. | |
| 4,855,238 A | 8/1989 | Gray et al. | |
| 4,925,793 A | 5/1990 | Goeddel et al. | |
| 4,929,544 A | 5/1990 | Vold | |
| 5,096,705 A | 3/1992 | Goeddel et al. | |
| 5,151,265 A | 9/1992 | Hwang-Felgner et al. | |
| 5,573,762 A | 11/1996 | Ferrara et al. | |
| 5,574,137 A | 11/1996 | Gray et al. | |
| 5,582,824 A | 12/1996 | Goeddel et al. | |
| 5,595,888 A | 1/1997 | Gray et al. | |
| 5,837,241 A | 11/1998 | Ferrara et al. | |
| 6,207,641 B1 * | 3/2001 | Torigoe et al. | |

FOREIGN PATENT DOCUMENTS

| EP | 790062 | 8/1997 |
|---|---|---|
| WO | WO 89/01341 | 2/1989 |
| WO | WO 90/03189 | 4/1990 |
| WO | WO 91/07984 | 6/1991 |

OTHER PUBLICATIONS

Lam XM et al. Pharm. Res. 14(6):725-729, 1997.*

Baehner, R.L., "Chronic Granulomatous Disease of Childhood: Clinical, Pathological, Biochemical, Molecular, and Genetic Aspects of the Disease" *Pediatric Pathol.* 10:143-153 (1990).
Betocchi et al., "Effects of Diltiazem on left ventricular systolic and diastolic function in hypertrophic cardiomyopathy" *Am. J. Cardiol.* 78:451-457 (1996).
Birks and Yacoub, "The role of nitric oxide and cytokines in heart failure" *Coronary Artery Diseases* 8:389-402 (1997).
Bonow et al., "Verapamil-induced improvement in left ventricular diastolic filling and increased exercise tolerance in patients with hypertrophic cardimyopathy: short- and long-term effects" *Circulation* 72:853-864 (1985).
Braunwald, E., "Pathophysiology of Heart Failure" *Heart Disease, A Textbook of Cardiovascular Medicine*, Third edition, W. B. Saunders Company pps. 426-448 (1988).
Caspari et al., "Collagen in the normal and hypertrophied human ventricle" *Cardiovasc. Res.* 11: 554-558 (1977).
Chien et al., "Regulation of Cardiac Gene Expression During Myocardial Growth and Hypertrophy: Molecular Studies of an Adaptive Physiologic Response" *FASEB J.* 5:3037-3046 (1991).
Chien et al., "Transcriptional Regulation During Cardiac Growth and Development" *Annu. Rev. Physiol.* 55:77-95 (1993).
De Maeyer, E., "The Presence and Possible Pathogenic Role of Interferons in Disease" *Interferons and other Regulatory Cytokines*, John Wiley and Sons Publishers, Chapter 16, pps. 380-424, (1988).
Ealick et al., "Three-Dimensional Structure of Recombinant Human Interferon-γ" *Science* 252:698-702 (1991.
Gray et al., "Expression of Human Immune Interferon cDNA in *E. coli* and Monkey Cells" *Nature* 295:503-508 (Feb. 11, 1982).
Harrison et al., "Effects of beta adrenergic blockade on the circulation, with particular reference to observations in patients with hypertrophic subaortic stenosis" *Circulation* 29:84-98 (1964).
Hattori et al., "Role and Nuclear Factor KB in cytokine-induced nitric oxide and tetrahydrobiopterin synthesis in rat neonatal cardiac myocytes" *J. Mol. Cell. Cardiol.* 29:1585-1592 (1997).
Hess et al., "Diastolic function and myocardial structure in patients with myocardial hypertrophy" *Circulation* 63:360-371 (1981).

(Continued)

*Primary Examiner*—Robert S. Landsman
(74) *Attorney, Agent, or Firm*—Janet E. Hasak, Esq.; Ginger R. Dreger, Esq.; Heller Ehrman, LLP

(57) ABSTRACT

The invention concerns the treatment of cardiac hypertrophy by interferon-gamma (IFN-γ). Cardiac hypertrophy may result from a variety of diverse pathologic conditions, including myocardial infarction, hypertension, hypertrophic cardiomyopathy, and valvular regurgitation. The treatment extends to all stages of the progression of cardiac hypertrophy, with or without structural damage of the heart muscle, regardless of the underlying cardiac disorder.

12 Claims, 12 Drawing Sheets

OTHER PUBLICATIONS

Inoue et al., "The Human Endothelin Family: Three Structurally and Pharmacologically Distinct Isopeptides Predicted by Three Separate Genes" *Proc. Natl. Acad. Sci. USA* 86:2863-2867 (Apr. 1989).

Katz, "Heart Failure" *Physiology of the Heart,* Katz, A.M., New York:Raven Press, Chapter 25, pps. 638-668, (1992).

Katz, A., "Scientific insights from clinical studies of converting-enzyme inhibitors in the failing heart" *Trends Cardiovasc. Med.* 5(1):37-44 (1995).

Kurzrock et al., "LIF: Not Just a Leukemia Inhibitory Factor" *Endocrine Reviews* 12(3):208-217 (1991).

Lorell et al., "Modification of abnormal left ventricular diastolic properties by nifedipine in patients with hypertrophic cardiomyopathy" *Circulation* 65:499-507 (1982).

Luss et al., "Characterization of inducible nitric oxide snythase expression in endotoxemic rat cardiacmyocytes in vivo and following cytokine exposure in vitro" *J. Mol. & Cell. Cardiol.* 27:2015-2029 (1995).

Metcalf, "Leukemia Inhibitory Factor—A Puzzling Polyfunctional Regulator" *Growth Factors* 7:169-173, (1992).

Morgan and Baker, "Cardiac Hypertrophy, Mechanical, Neural and Endocrine Dependence" *Circulation* 83:13-25 (1991).

Pearlman et al., "Muscle fiber orientation and connective tissue content in the hypertrophied human heart" *Lab. Invest* 46:158-164 (1982).

Pennica et al., "Expression Cloning of Cardiotrophin 1, a Cytokine That Induces Cardiac Myocyte Hypertrophy" *Proceedings of the National Academy of Sciences, USA* 92:1142-1146 (Feb. 1995).

Pinsky et al., "The lethal effects of cytokine-induced nitric oxide on cardiac myocytes are blocked by nitric oxide synthase antagonism or transforming growth factor β" *J. Clin. Invest* 95:677-685, (1995).

Pollick, C., "Muscular subaortic stenosis, hemodynamic and clinical improvement after disopyramide" *New England J. of Medicine* 307 (16):997-999 (1982).

Rossi et al., "Effect of captopril on the prevention and regression of myocardial cell hypertrophy and interstitial fibrosis in pressure overload cardiac hypertrophy" *Am. Heart J.* 124:700-709 (1992).

Schwarz et al., "Correlation between myocardial structure and diastolic properties of the heart in chronic aortic valve disease: effects of corrective surgery" *Am. J. Cardiol.* 42:895-903 (1978).

Shahi et al., "Regression of hypertensive left ventricular hypertrophy and left ventricular diastolic function" *Lancet* 336:458-461 (1990).

Singh et al., "Glucocorticoids increase osteopontin expression in cardiac myocytes and microvascular endothelial cells" *Journal of Biological Chemistry* 270:28471-28478 (1995).

Szlachcic et al., "Effects of diltiazem on left ventricular mass and diastolic filling in mild to moderate hypertension" *Am. J. Cardiol.* 63 : 198-201 (1989).

Taniguchi et al., "Human leukocyte and fibroblast interferons are structurally related" *Nature* 285:547-549 (1980).

Thompson et al. "Effects of propranolol on myocardial oxygen consumption, substrate extraction, and haemodynamics in hypertrophic obstructive cardiomyopathy" *Br. Heart J.* 44:488-98 (1980).

Ungureanu-Longrois et al., "Induction of nitric oxide synthase activity by cytokines in ventricular myocytes is necessary but not sufficient to decrease contractile responsiveness to γ-adrenergic agonists" *Circ. Res.* 77:494-502 (1995).

Wigle et al., "Hypertrophic cardiomyopathy, clinical spectrum and treatment" *Circulation* 92:1680-1692 (1995).

Yanagisawa and Masaki, "Molecular Biology and Biochemistry of the Endothelins" *Trends Pharm. Sci.* 10: 374-378 (Sep. 1989).

Adams et al., "Prostaglandin $F_{2\alpha}$ stimulates hypertrophic growth of cultured neonatal rat ventricular myocytes" *Journal of Biological Chemistry* 271 (2):1179-1186 (Jan. 12, 1996).

Anversa and Kajstura, "Ventricular myocytes are not terminally differentiated in the adult mammalian heart" *Circulation Research* 83 (1):1-14 (Jul. 13, 1998).

Hansson and Holm, "Interferon-γ inhibits arterial stenosis after injury" *Circulation* 84(3):1266-1272 (Sep. 1991).

Hansson et al., "Immune mechanisms in atherosclerosis" *Arteriosclerosis* 9(5):567-578 (Sep.-Oct. 1989).

Pulkki K., "Cytokines and cardiomyocyte death" *Annals of Medicine* 29 (4): 339-343 (Aug. 1997).

Shimokado et al., "Bidirectional regulation of smooth muscle cell proliferation by IFN-γ" *Journal of Atherosclerosis and Thrombosis* 1 (Suppl. 1):S29-S33 (1994).

Soonpaa and Field, "Survey of studies examining mammalian cardiomyocyte DNA synthesis" *Circulation Research* 83(1):15-26 (Jul. 13, 1998).

Stein et al., "Involvement of nitric oxide in IFN-γ-mediated reduction of microvessel smooth muscle cell proliferation" *Molecular Immunology* 32(13):965-973 (Sep. 1995).

Stopeck et al., "Transfer and expression of the interferon gamma gene in human endothelial cells inhibits vascular smooth muscle cell growth in vitro" *Cell Transplantation* 6(1) : 1-8 (Jan.-Feb. 1997).

Sugden, P., "Signaling in myocardial hypertrophy: life after calcineurin?" *Circulation Research* 84(6):633-646 (Apr. 2, 1999).

Thaik et al., "Effects of inflammatory cytokines on growth and growth factor expression in cardiac myocytes and fibroblasts" *Circulation* (abstract no. 2723 from the 68th Scientific Session of the American Heart Association held in Anaheim, CA on Nov. 13-16, 1995) 92(8 Suppl.): 1569 (1995).

Warner et al., "Immune interferon inhibits proliferation and induces 2'-5' - oligoadenylate synthetase gene expression in human vascular smooth muscle cells" *Journal of Clinical Investigation* 83 (4):1174-118 (Apr. 1989).

Yamamoto et al., "Effects of intranasal administration of recombinant murine interferon-γ on murine acute myocarditis caused by encephalomyocarditis virus" *Circulation* 97(10):1017-1023 (Mar. 17, 1998).

Yang et al., "Interferon-γ attenuates cardiac hypertrophy in a rat model of pressure overload" *Circulation* (abstract No. 1704) 98(17):1704 (Oct. 27. 1998).

Tellides et al., "Interferon-γ elicits arteriosclerosis in the absence of leukocytes" *Nature* 403:207-211 (Jan. 2000).

* cited by examiner

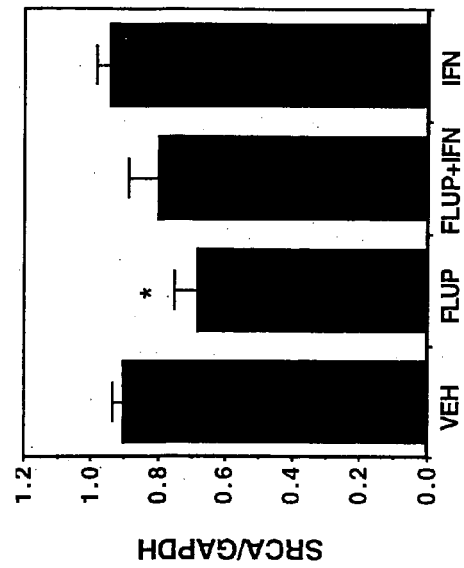
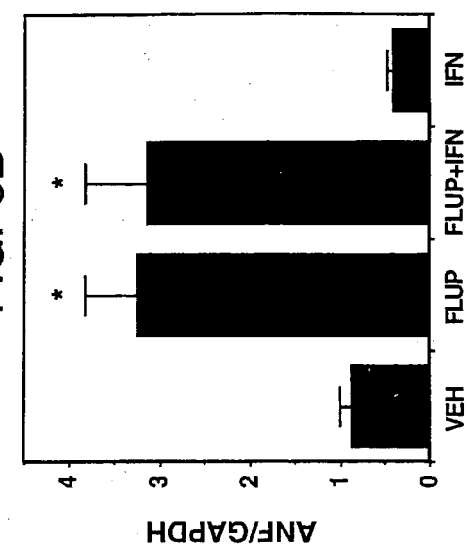
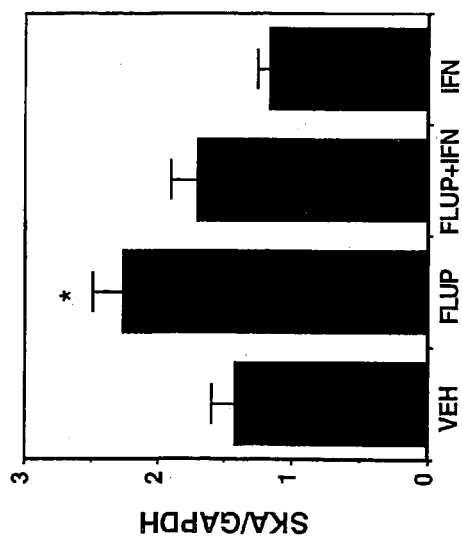
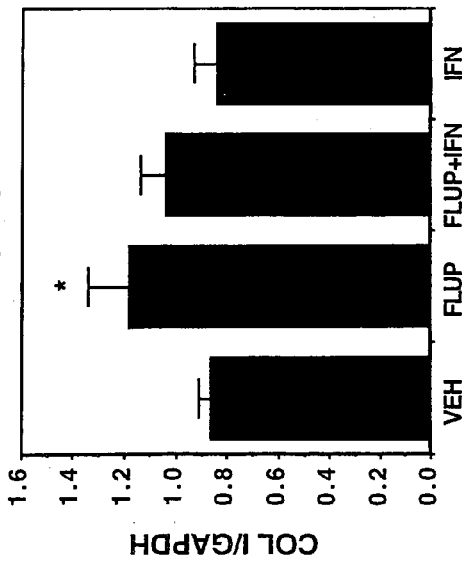
FIG. 6A
FIG. 6B
FIG. 6C
FIG. 6D

METHODS FOR TREATING CARDIAC HYPERTROPHY BY ADMINISTERING IFN-γ

This is a continuation of application Ser. No. 09/273,099 filed on Mar. 19, 1999, now U.S. Pat. No. 6,187,304, which claims priority of provisional application Ser. No. 60/080,448 filed on Apr. 2, 1998.

RELATED APPLICATION

This application is a non-provisional application filed under 37 CFR 1.53(b)(1), claiming priority under 35 USC 119(e) to provisional application No. 60/080,448 filed 2 Apr. 1998, the contents of which are incorporated herein by reference.

FIELD OF THE INVENTION

The present invention relates generally to the effects of IFN-γ on cardiac hypertrophy. More particularly, the invention concerns the use of IFN-γ for the prevention and treatment of cardiac hypertrophy and associated pathological conditions.

BACKGROUND OF THE INVENTION

Interferon-Gamma (IFN-γ)

Interferons are relatively small, single-chain glycoproteins released by cells invaded by viruses or certain other substances. Interferons are presently grouped into three major classes, designated leukocyte interferon (interferon-alpha, α-interferon, IFN-α), fibroblast interferon (interferon-beta, β-interferon, IFN-β), and immune interferon (interferon-gamma, γ-interferon, IFN-γ). In response to viral infection, lymphocytes synthesize primarily α-interferon (along with a lesser amount of a distinct interferon species, commonly referred to as omega interferon), while infection of fibroblasts usually induces β-interferon. α- and β-interferons share about 20–30 percent amino acid sequence homology. The gene for human IFN-β lacks introns, and encodes a protein possessing 29% amino acid sequence identity with human IFN-αI, suggesting that IFN-α and IFN-β genes have evolved from a common ancestor (Taniguchi et al., Nature 285, 547–549 [1980]). By contrast, IFN-γ is not induced by viral infection, rather, is synthesized by lymphocytes in response to mitogens, and is scarcely related to the other two types of interferons in amino acid sequence. Interferons-α and -β are known to induce MHC Class I antigens, while IFN-γ induces MHC Class II antigen expression, and also increases the efficiency with which target cells present viral peptide in association with MHC Class I molecules for recognition by cytotoxic T cells.

IFN-γ is a member of the interferon family, which exhibits the antiviral and anti-proliferative properties characteristic of interferons-α and -β (IFN-α and IFN-β) but, in contrast to those interferons, is PH 2 labile. IFN-γ was originally produced upon mitogenic induction of lymphocytes. The recombinant production of human IFN-γ was first reported by Gray, Goeddel and co-workers (Gray et al., Nature 295, 503–508 [1982]), and is subject of U.S. Pat. Nos. 4,762,791, 4,929,544, 4,727,138, 4,925,793, 4,855,238, 5,582,824, 5,096,705, 5,574,137, and 5,595,888. The recombinant human IFN-γ of Gray and Goeddel as produced in E. coli, consisted of 146 amino acids, the N-terminal position of the molecule commencing with the sequence CysTyrCys. It has later been found that the native human IFN-γ (i.e., that arising from mitogen induction of human peripheral blood lymphocytes and subsequent purification) is a polypeptide which lacks the CysTyrCys N-terminus assigned by Gray et al., supra. More recently, the crystal structure of E. coli derived recombinant human IFN-γ (rhIFN-γ) was determined (Ealick et al., Science 252, 698–702 [1991]), showing that the protein exists as a tightly intertwined non-covalent homodimer, in which the two identical polypeptide chains are oriented in an antiparallel manner.

IFN-γ is known to exhibit a broad range of biological activities, including antitumor, antimicrobial and immunoregulatory activities. A particular form of recombinant human IFN-γ (rhIFN-γ-1b, Actimmune®, Genentech, Inc. South San Francisco, Calif.) is commercially available as an immunomodulatory drug for the treatment of chronic granulomatous disease characterized by severe, recurrent infections of the skin, lymph nodes, liver, lungs, and bones due to phagocyte disfunction (Baehner, R. L., Pediatric Pathol. 10, 143–153 [1990]). IFN-γ has also been proposed for the treatment of atopic dermatitis, a common inflammatory skin disease characterized by severe pruritus, a chronically relapsing course with frequent periods of exacerbation, a distinctive clinical morphology and distribution of skin lesions (see PCT Publication No. WO 91/07984 published 13 Jun. 1991), vascular stenosis, including the treatment of restenosis following angioplasty and/or vascular surgery (PCT Publication No. WO 90/03189 published 5 Apr. 1990), various lung conditions, including respiratory distress syndromes (RDS), such as adult respiratory distress syndrome (ARDS) and a neonatal form, termed variously as idiopathic RDS or hyaline membrane disease (PCT Publication No. WO 89/01341, published 23 Feb. 1989). In addition, IFN-γ has been proposed for use in the treatment of various allergies, e.g. asthma, and HIV-infection-related conditions, such as opportunistic infections, e.g. Pneumocystis carinii pneumonia, and trauma-associated sepsis. Impaired IFN-γ production has been observed in multiple-sclerosis (MP) patients, and it has been reported that the production of IFN-γ is greatly suppressed in suspensions of mitogen-stimulated mononuclear cells derived from AIDS patients. For a review see, for example, Chapter 16, "The Presence of Possible Pathogenic Role of Interferons in Disease", In: Interferons and other Regulatory Cytokines, Edward de Maeyer (1988, John Wilet and Sons Publishers).

Interferon-γ, along with other cytokines, has been implicated as an inducer of inducible nitric oxide (iNOS) which, in turn, has been described as an important mediator of the inflammatory mechanism underlying heart failure, of the cardiac response to sepsis or allograft rejection, as well as the progression of dilated cardiomyopathies of diverse etiologies. Ungureanu-Longrois et al., Circ. Res. 77, 494–502 (1995); Pinsky et al., J. Clin. Invest. 95, 677–685 (1995); Singh et al., J. Biol. Chem. 270, 28471–8 (1995); Birks and Yacoub, Coronary Artery Disease 8, 389–402 (1997); Hattori et al., J. Mol. Cell. Cardiol. 29, 1585–92 (1,997). Indeed, IFN-γ has been reported to be the most potent single cytokine with regard to myocyte iNOS induction (Watkins et al., J. Mol. & Cell. Cardiol. 27, 2015–29 [1995]).

Cardiac Hypertrophy

Hypertrophy is generally defined as an increase in size of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both.

Cardiac hypertrophy is the enlargement of heart that is activated by both mechanical and hormonal stimuli and enables the heart to adapt to demands for increased cardiac output or to injury. Morgan and Baker, *Circulation* 83, 13–25 (1991). This response is frequently associated with a variety of distinct pathological conditions, such as hypertension, aortic stenosis, myocardial infarction, cardiomyopathy, valvular regurgitation, cardiac shunt, congestive heart failure, etc.

On a cellular level, the heart functions as a syncytium of myocytes and surrounding support cells, called non-myocytes. While non-myocytes are primarily fibroblast/mesenchymal cells, they also include endothelial and smooth muscle cells. Indeed, although myocytes make up most of the adult myocardial mass, they represent only about 30% of the total cell numbers present in heart.

The enlargement of embryonic heart is largely dependent on an increase in myocyte number, which continues until shortly after birth, when cardiac myocytes lose their proliferative capacity. Further growth occurs through hypertrophy of the individual cells. Hypertrophy of adult cardiac ventricular myocytes is a response to a variety of conditions which lead to chronic hemodynamic overload. Thus, in response to hormonal, physiological, hemodynamic, and pathological stimuli, adult ventricular muscle cells can adapt to increased workloads through the activation of a hypertrophic process. This response is characterized by an increase in myocyte cell size and contractile protein content of individual cardiac muscle cells, without concomitant cell division and activation of embryonic genes, including the gene for atrial natriuretic peptide (ANP). Chien et al., *FASEB J.* 5, 3037–3046(1991); Chien et al., *Annu. Rev. Physiol.* 55, 77–95 (1993). An increment in myocardial mass as a result of an increase in myocyte size that is associated with an accumulation of interstitial collagen within the extracellular matrix and around intramyocardial coronary arteries has been described in left ventricular hypertrophy secondary to pressure overload in humans (Caspari et al., *Cardiovasc. Res.* 11, 554–8 [1977]; Schwarz et al., *Am. J. Cardiol.* 42, 895–903 [1978]; Hess et al., *Circulation* 63, 360–371 [1981]; Pearlman et al., *Lab. Invest.* 46, 158–164 [1982]). Cardiac hypertrophy due to chronic hemodynamic overload is the common end result of most cardiac disorders and a consistent feature of cardiac failure.

It has also been suggested that paracrine factors produced by non-myocyte supporting cells may additionally be involved in the development of cardiac hypertrophy, and various non-myocyte derived hypertrophic factors, such as, leukocyte inhibitory factor (LIF) and endothelin, have been identified. Metcalf, *Growth Factors* 7, 169–173 (1992); Kurzrock et al., *Endocrine Reviews* 12, 208–217 (1991); Inoue et al., *Proc. Natl. Acad. Sci. USA* 86: 2863–2867 (1989); Yanagisawa and Masaki, *Trends Pharm. Sci.* 10, 374–378 (1989); U.S. Pat. No. 5,573,762 (issued Nov. 12, 1996). Further exemplary factors that have been identified as potential mediators of cardiac hypertrophy include cardiotrophin-1 (CT-1) (Pennica et al., *Proc. Nat. Acad. Sci. USA* 92:1142–1146 [1995]), catecholamines, adrenocorticosteroids, angiotensin, and prostaglandins.

Adult myocyte hypertrophy is initially beneficial as a short term response to impaired cardiac function by permitting a decrease in the load on individual muscle fibers. With severe, long-standing overload, however, the hypertrophied cells begin to deteriorate and die. Katz, "Heart Failure", in: Katz A. M. ed., Physiology of the Heart (New York, Raven Press, 1992) pp. 638–668. Cardiac hypertrophy is a significant risk factor for both mortality and morbidity in the clinical course of heart failure. Katz, *Trends Cardiovasc. Med.* 5, 37–44 (1995).

For further details of the causes and pathology of cardiac hypertrophy see, e.g. Heart Disease, A Textbook of Cardiovascular Medicine, Braunwald, E. ed., W.B. Saunders Co., 1988, Chapter 14, Pathophysiology of Heart Failure.

Treatment of Cardiac Hypertrophy

At present, the treatment of cardiac hypertrophy varies depending on the underlying cardiac disease. Catecholamines, adrenocorticosteroids, angiotensin, prostaglandins, leukemia inhibitory factor (LIF), endothelin (including endothelin-1, -2, and -3 and big endothelin), cardiotrophin-1 (CT-1) and cardiac hypertrophy factor (CHF) are among the factors identified as potential mediators of hypertrophy.

For example, $\beta$-adrenergic receptor blocking drugs ($\beta$-blockers, e.g., propranolol, timolol, tertalolol, carteolol, nadolol, betaxolol, penbutolol, acetobutolol, atenolol, metoprolol, carvedilol, etc.) and verapamil have been used extensively in the treatment of hypertrophic cardiomyopathy. The beneficial effects of $\beta$-blockers on symptoms (e.g. chest pain) and exercise tolerance are largely due to a decrease in the heart rate with a consequent prolongation of diastole and increased passive ventricular filling. Thompson et al., *Br. Heart J.* 44, 488–98 (1980); Harrison et al., *Circulation* 29, 84–98 (1964). Verapamil has been described to improve ventricular filling and probably reducing myocardial ischemia. Bonow et al., *Circulation* 72, 853–64 (1985). Nifedipine and diltiazem have also been used occasionally in the treatment of hypertrophic cardiomyopathy. Lorell et al., *Circulation* 65, 499–507 (1982); Betocchi et al., *Am. J. Cardiol.* 78, 451–7 (1996). However, because of its potent vasodilating properties, nifedipine may be harmful, especially in patients with outflow obstruction. Disopyramide has been used to relieve symptoms by virtue of its negative inotropic properties. Pollick, *N. Engl. J. Med.* 307, 997–9 (1982). In many patients, however, the initial benefits decrease with time. Wigle et al., *Circulation* 92, 1680–92 (1995).

Antihypertensive drug therapy has been reported to have beneficial effects on cardiac hypertrophy associated with elevated blood pressure. Examples of drugs used in antihypertensive therapy, alone or in combination, are calcium antagonists, e.g. nitrendipine; $\beta$-adrenergic receptor blocking agents, e.g., those listed above; angiotensin converting enzyme (ACE) inhibitors, e.g., quinapril, captopril, enalapril, ramipril, benazepril, fosinopril, lisinopril; diuretics, e.g. chorothiazide, hydrochlorothiazide, hydroflumethazide, methylchlothiazide, benzthiazide, dichlorphenamide, acetazolamide, indapamide; calcium channel blockers, e.g. diltiazem, nifedipine, verapamil, nicardipine. For example, treatment of hypertension with diltiazem and captopril showed a decrease in left ventricular muscle mass, but the Doppler indices of diastolic function did not normalize. Szlachcic et al., *Am. J. Cardiol.* 63, 198–201 (1989); Shahi et al., *Lancet* 336, 458–61 (1990). These findings were interpreted to indicate that excessive amounts of interstitial collagen may remain after regression of left ventricular hypertrophy. Rossi et al., *Am. Heart J.* 124, 700–709 (1992). Rossi et al., supra, investigated the effect of captopril on the prevention and regression of myocardial cell hypertrophy and interstitial fibrosis in pressure overload cardiac hypertrophy, in experimental rats.

As there is no generally applicable therapy for the treatment of cardiac hypertrophy, the identification of factors that can prevent or reduce cardiac myocyte hypertrophy is of primary importance in the development of new therapeutic strategies to inhibit pathophysiological cardiac growth.

SUMMARY OF THE INVENTION

We have unexpectedly found that IFN-γ inhibits the prostaglandin $F_{2\alpha}$ ($PGF_{2\alpha}$)- and phenylephrine-induced spreading of cardiac myocytes isolated from adult rats. We have further found that IFN-γ inhibits in vivo both cardiac hypertrophy induced by fluprostenol, an agonist analog of $PGF_{2\alpha}$, and hypertrophy induced by pressure overload in a rat model.

Accordingly, the present invention concerns the treatment of cardiac hypertrophy, regardless of the underlying cause, by administering a therapeutically effective dose of IFN-γ. If the objective is the treatment of human patients, IFN-γ preferably is recombinant human IFN-γ (rhIFN-γ), most preferably, rhIFN-γ-1b, which will be defined hereinbelow. The concept of treatment is used in the broadest sense, and specifically includes the prevention (prophylaxis), moderation, reduction, and curing of cardiac hypertrophy of any stage.

IFN-γ preferably is administered in the form of a liquid pharmaceutical formulation, which may be preserved to achieve extended storage stability. Preserved liquid pharmaceutical formulations might contain multiple doses of IFN-γ, and might, therefore, be suitable for repeated use.

IFN-γ might be administered in combination with one or more further therapeutic agent used for the treatment of cardiac hypertrophy, or a physiological condition instrumental in the development of cardiac hypertrophy, such as elevated blood pressure, aortic stenosis, or myocardial infarction.

The invention further concerns a method for making a pharmaceutical composition for the treatment of cardiac hypertrophy, which comprises IFN-γ as an active ingredient.

The invention also concerns a pharmaceutical product which comprises:

(a) a pharmaceutical composition comprising at least one therapeutically effective dosage of IFN-γ;
(b) a container containing said pharmaceutical composition; and
(c) a label affixed to said container, or a package insert included in said pharmaceutical product referring to the use of said IFN-γ in the treatment of cardiac hypertrophy.

BRIEF DESCRIPTION OF THE FIGURES

In the Figures and throughout the examples, "IFN" or "IFN-γ" refers to recombinant mouse IFN-γ (Genentech, Inc., South San Francisco, Calif., or Genzyme, Cambridge, Mass.).

FIGS. 6A–6D Bargraphs showing the effect of fluprostenol (FLUP) and IFN-γ on: A Skeletal actin (SKA); B Sarcoplasmic reticulum calcium ATPase (SRCA); C Collagen I (COL I); D Atrial natriuretic factor (ANF) expression. Expression levels are normalized to glyceraldehyde-3-phosphate dehydrogenase (GAPDH) message. VEH is vehicle. There were 7 animals per group and the data are presented as the mean±SEM. P<0.05 vs VEH group.

DETAILED DESCRIPTION OF THE INVENTION

A. Definitions

Figure 1A:
FIGS. 1A–1F Inhibition of prostaglandin $F_{2\alpha}$ ($PGF_{2\alpha}$)-induced spreading response by IFN-γ. Myocytes were pre-incubated with saline vehicle or IFN-γ (500 U/ml) on day of isolation. A second addition of vehicle or IFN-γ was performed 24h after isolation, along with the addition of either vehicle or $PGF_{2\alpha}$ ($10^{-7}$ M). After an additional 72 hr incubation, cells were fixed in glutaraldehyde, stained with eosin Y and viewed by fluorescence microscopy. A, B, C Cardiac myocytes after 4 days in culture: control, $PGF_{2\alpha}$, and $PGF_{2\alpha}$+IFN-γ, respectively. D, E, F Histographs showing maximum breadth of rod shaped cardiac myocytes versus percent frequency of breadth occurrence. The maximum breadth of rod-shaped cells was determined by fluorescence microscopy and imaging software. At least 200 rod shaped cells from a single experiment were examined per group. IFN-γ alone had no observable effect on the morphology of the cells. P<0.001 for all group comparisons.
Figure 1B:
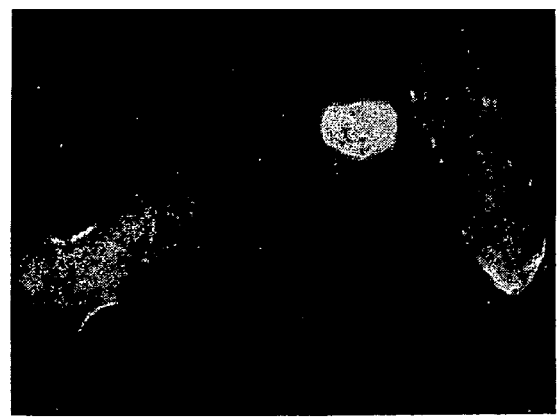
Figure 1C:
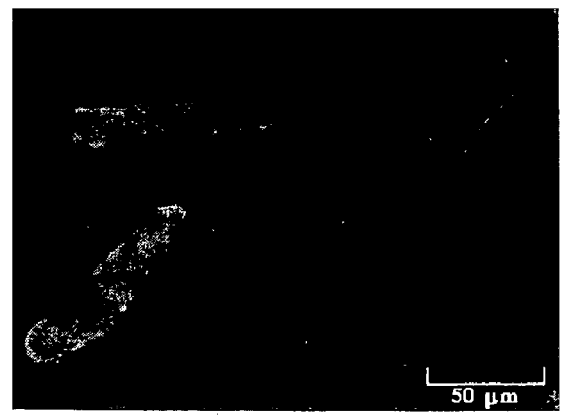
Figure 1D:
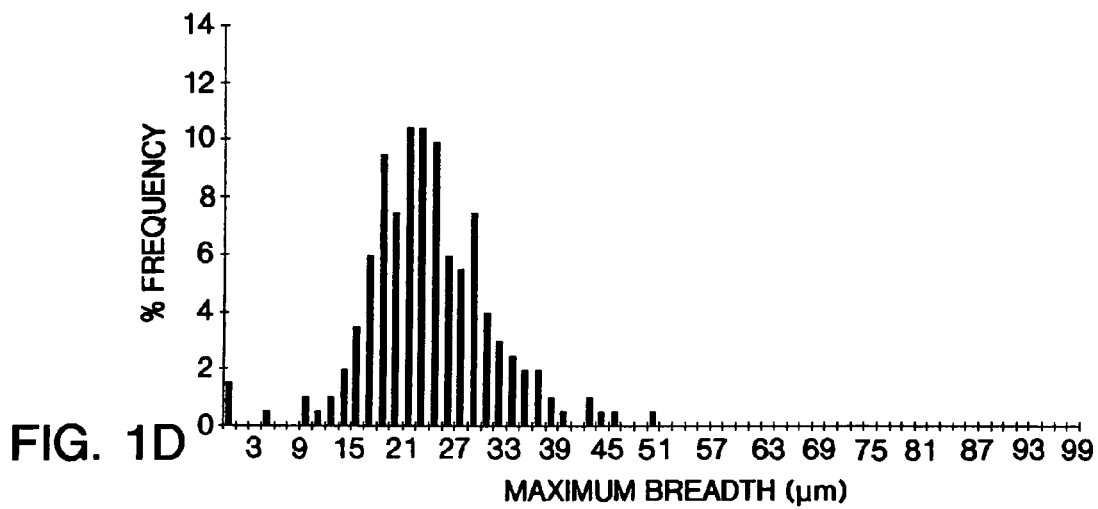
Figure 1E:
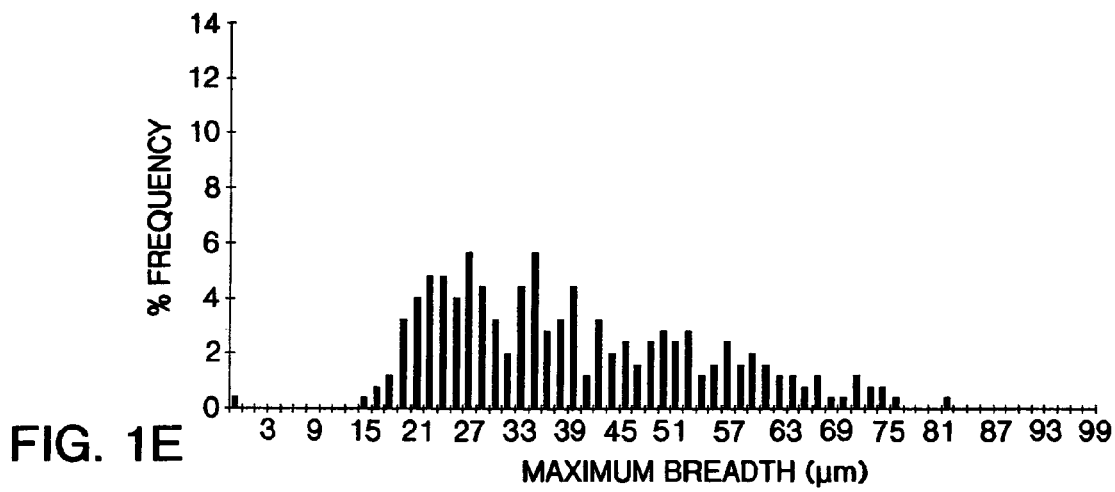
Figure 1F:
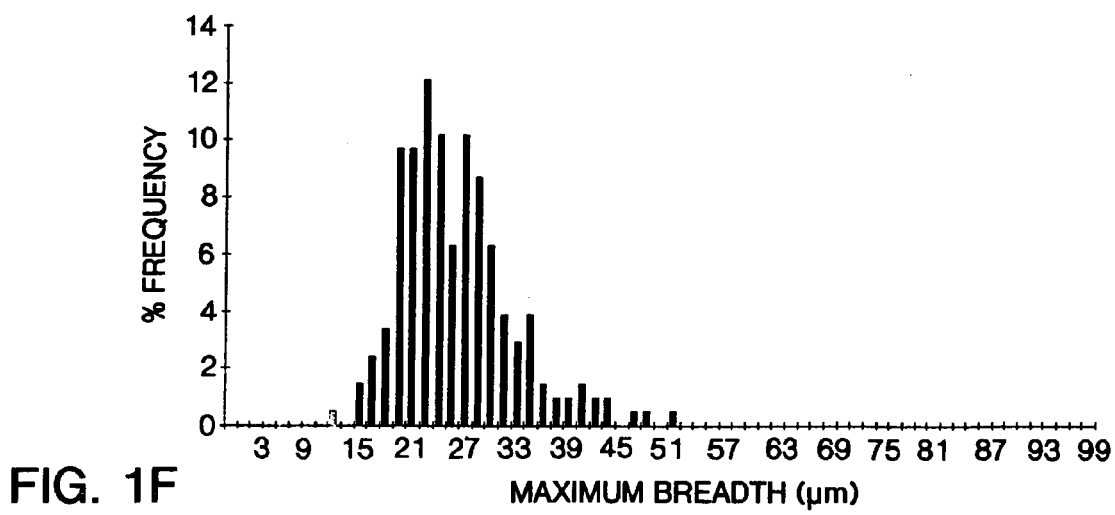
Figure 2A:
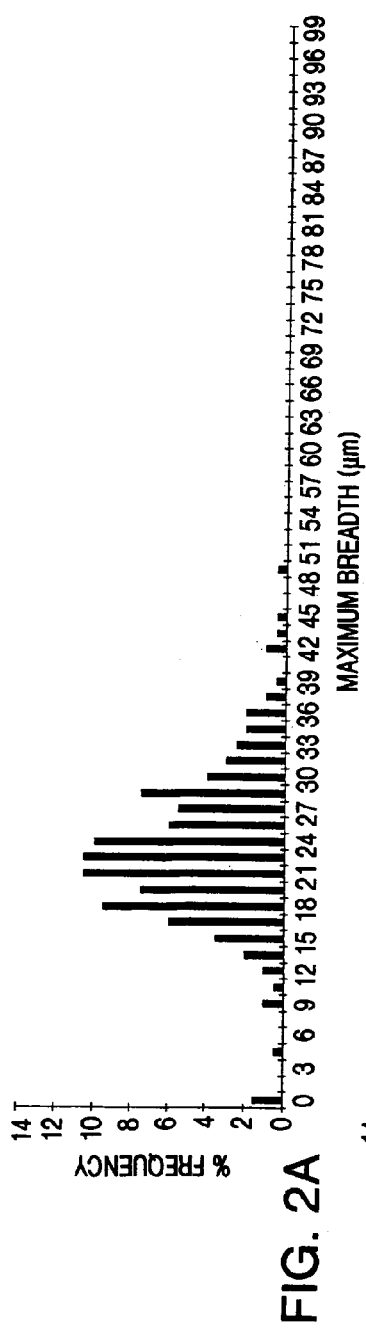
FIGS. 2A–2E Dose responsive inhibition of $PGF_{2\alpha}$-induced response by IFN-γ (500–25 U/ml). Myocytes were pre-incubated with saline vehicle or IFN-γ on day of isolation. A second amount of IFN-γ was added 24 hr after isolation, along with the addition of either vehicle or $PGF_{2\alpha}$ ($10^{-7}$ M). After an additional 72 hr incubation, cells were fixed in glutaraldehyde, stained with eosin Y and viewed under fluorescence. Quantitation of myocyte morphology: A control, B $PGF_{2\alpha}$, C $PGF_{2\alpha}$+IFN-γ (25 U/ml), D $PGF_{2\alpha}$+IFN-γ (100 U/ml), E $PGF_{2\alpha}$+IFN-γ (500 U/ml). Histographs showing maximum breadth of rod shaped cardiac myocytes versus percent frequency of breadth occurrence. The maximum breadth of rod-shaped cells was determined by fluorescence microscopy and imaging software. At least 200 rod shaped cells from a single experiment were examined per group. IFN-γ alone had no observable effect on the morphology of the cells. P<0.001 for all group comparisons.
Figure 2B:
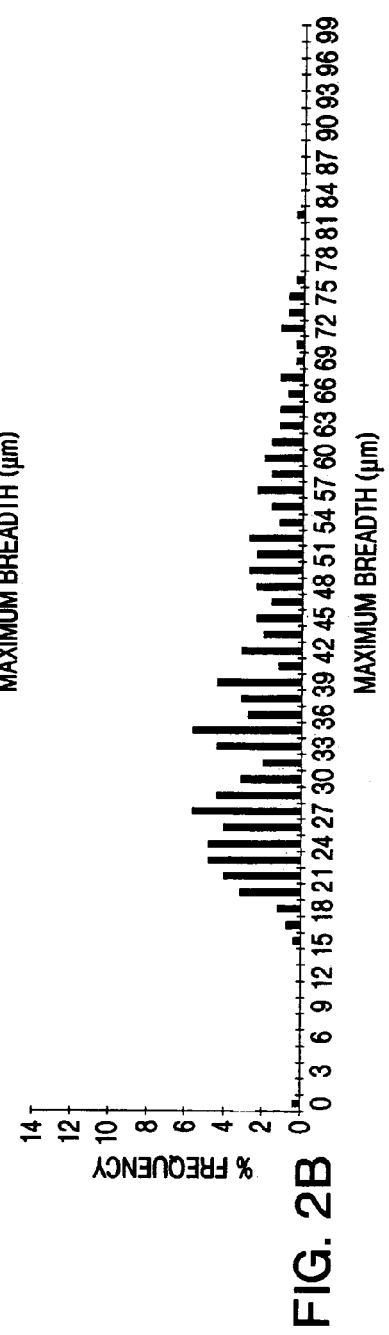
Figure 2C:
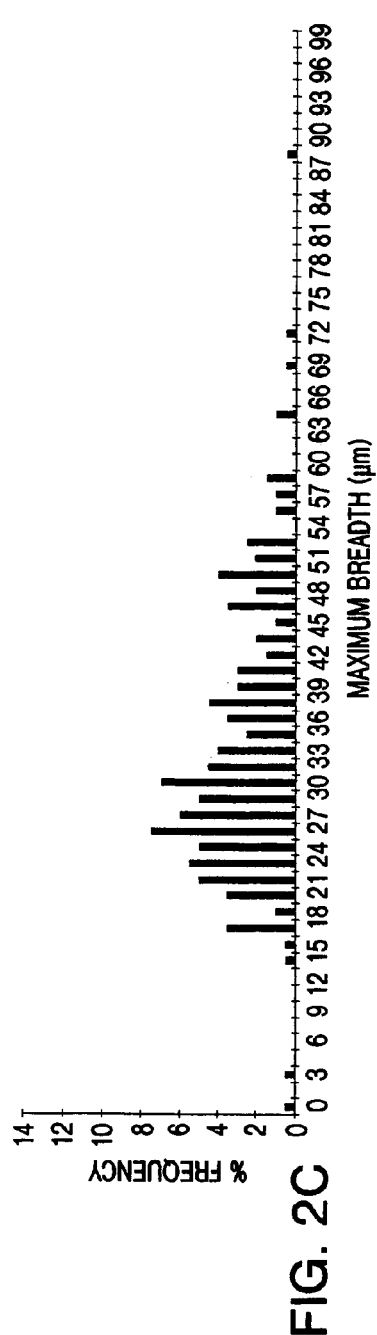
Figure 2D:
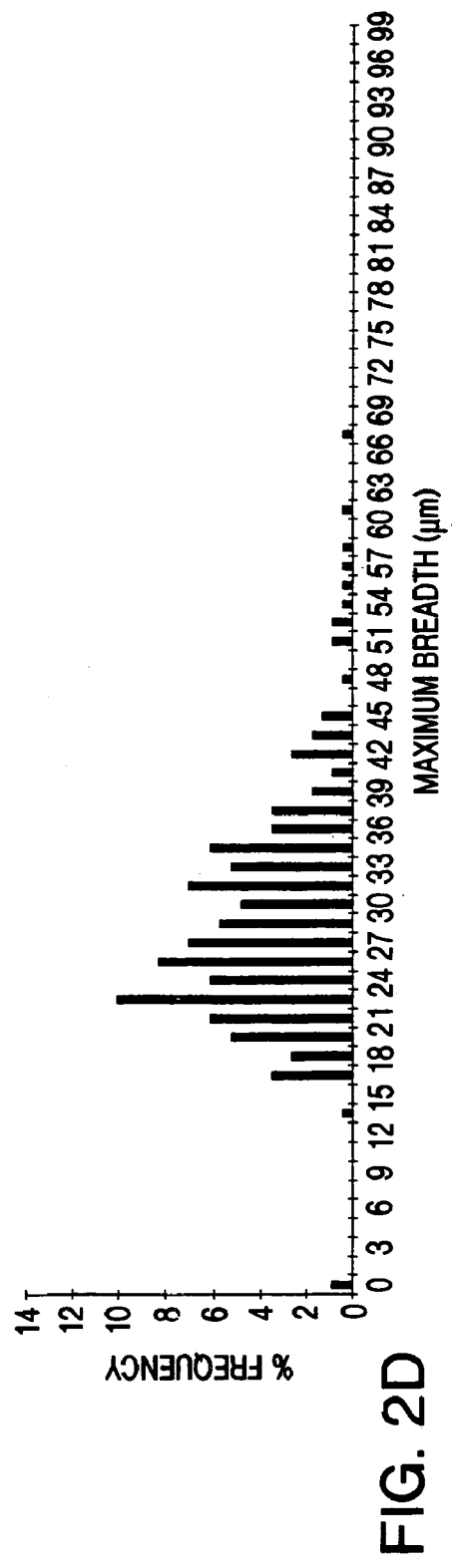
Figure 2E:
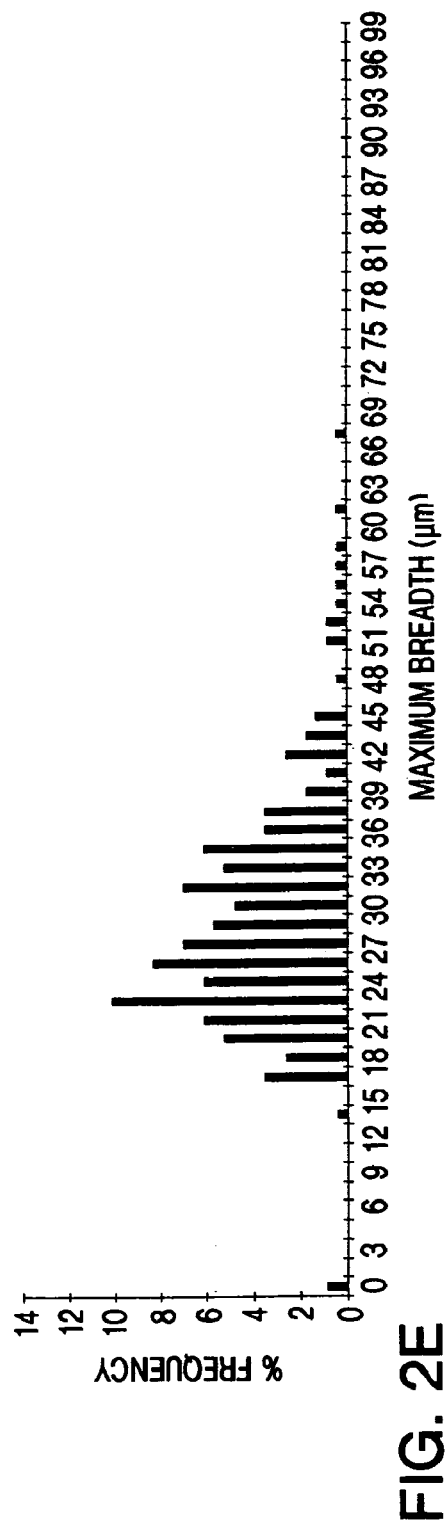
Figure 3A:
FIGS. 3A–3F Inhibition of phenylephedrine (PE)-induced spreading response by IFN-γ. Myocytes were pre-incubated with saline vehicle or IFN-γ (500 U/ml) on day of isolation. A second addition of vehicle or IFN-γ was performed 24h after isolation, along with the addition of either vehicle or PE ($10^{-5}$ M). After an additional 72 hr incubation, cells were fixed in glutaraldehyde, stained with eosin Y and viewed by fluorescence microscopy. A, B, C Cardiac myocytes after 4 days in culture: control, PE, and PE+IFN-γ, respectively. D, E, F Histographs showing maximum breadth of rod shaped cardiac myocytes versus percent frequency of breadth occurrence. The maximum breadth of rod-shaped cells was determined by fluorescence microscopy and imaging software. At least 200 rod shaped cells from a single experiment were examined per group. IFN-γ alone had no observable effect on the morphology of the cells. P<0.001 for all group comparisons.
Figure 3B:
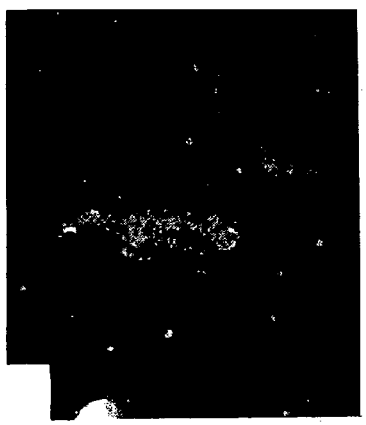
Figure 3C:
Figure 3D:
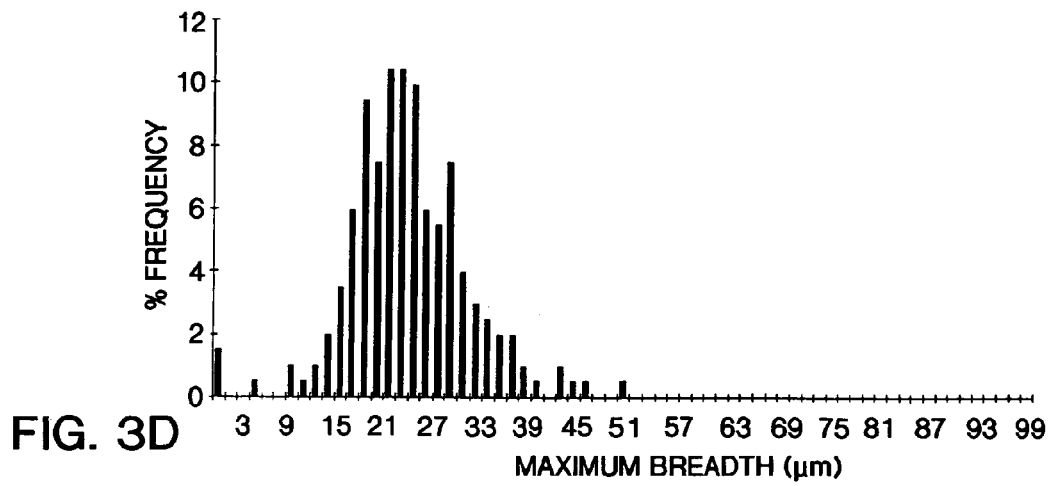
Figure 3E:
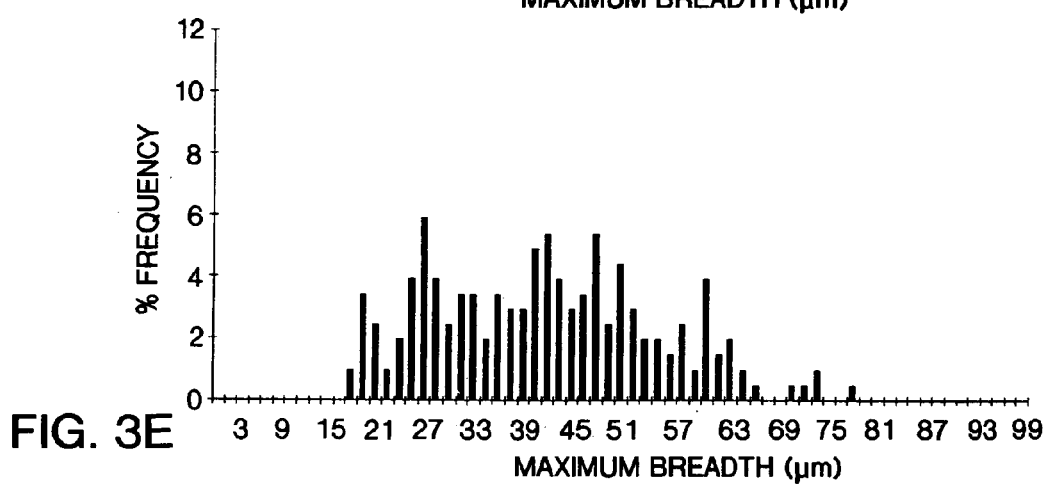
Figure 3F:
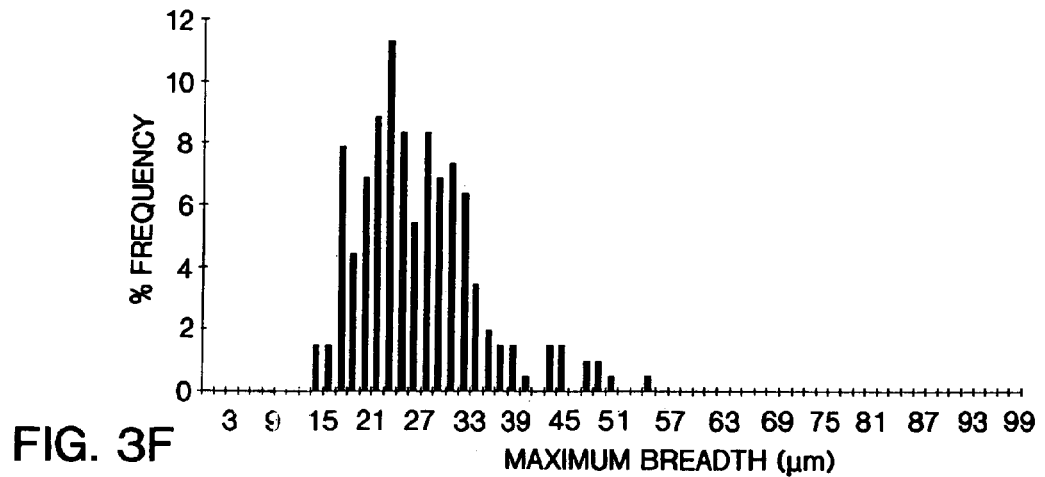

"Gamma interferon", "interferon-gamma", or "IFN-γ" refers variously to all forms of (human and non-human animal) gamma interferon that are shown to be biologically active in any assay of cardiac hypertrophy, e.g. the hypertrophy assays disclosed herein, and is meant to include, but is not limited to, mature, pro, met and/or des(1–3) (also referred to as desCysTyrCys IFN-γ) form, whether obtained from natural source, chemically synthesized or produced by techniques of recombinant DNA technology. A complete description of the preparation of recombinant human IFN-γ (rhuIFN-γ) including its cDNA and amino acid sequences are disclosed, for example, in U.S. Pat. Nos. 4,727,138; 4,762,791; 4,925,793; 4,929,554; 5,582,824; 5,096,705; 4,855,238; 5,574,137; and 5,595,888. CysTyrCys-lacking recombinant human IFN-γ, including variously truncated derivatives are, for example, disclosed in European Patent Publication No. 146,354. Non-human animal interferons, including IFN-γ, are, for example, disclosed in European Publication No. 88,622. The term includes variously glycosylated forms and other variants (e.g. amino acid sequence variants) and derivatives of such native (wild-type) interferons, whether known in the art or will become available in the future. Examples of such variants are alleles, and the products of site-directed mutagenesis in which residues are deleted, inserted and/or substituted (see, e.g. European Publication No. 146,354 referred to above). IFN-γ is known to have a narrow host range, therefore, IFN-γ homologous to the animal to be treated should be used. In human therapy, the desCysTyrCys variant of the sequence shown in U.S. Pat. No. 4,717,138 and its counterpart EP 77,670, is preferably employed, and optionally the C-terminal variant in which the last four amino acid residues are deleted in post-translational processing. For human therapeutic use, the IFN-γ of the present invention preferably is recombinant human IFN-γ (rhIFN-γ), with or without the amino acids CysTyrCys at the N-terminus. More preferably, IFN-γ is a recombinant human IFN-γ species (recombinant human interferon gamma-1b, rhIFN-γ-1b, containing 140 amino acids), which is the active ingredient of the commercial formulation, Actimmune® (Genentech, Inc., South San Francisco, Calif.). As IFN-γ is known to be highly species specific, in animal experiments, or for veterinary use. IFN-γ of the animal species to be treated is preferably employed. Thus, in the in vivo experiments using a rat animal model, murine (mouse) recombinant IFN-γ (Genentech, Inc.) has been employed. Rat and mice and sufficiently closely related to permit the use of mouse IFN-γ in a rat model.

In a pharmacological sense, in the context of the present invention, a "therapeutically effective amount" of IFN-γ refers to an amount effective in the treatment of hypertrophy, specifically cardiac hypertrophy.

"Hypertrophy", as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth. Accordingly, "cardiac hypertrophy" is defined as an increase in mass of the heart, which, in adults, is characterized by an increase in myocyte cell size and contractile protein content without concomitant cell division. The character of the stress responsible for inciting the hypertrophy, (e.g., increased preload, increased afterload, loss of myocytes, as in myocardial infarction, or primary depression of contractility), appears to play a critical role in determining the nature of the response. The early stage of cardiac hypertrophy is usually characterized morphologically by increases in the size of mycrofibrils and mitochondria, as well as enlargement of mitochondria and nuclei. At this stage, while muscle cells are larger than normal, cellular organization is largely preserved. At a more advanced stage of cardiac hypertrophy, there are preferential increases in the size or number of specific organelles, such a mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase "cardiac hypertrophy" is used to include all stages of the progression of this condition, characterized by various degrees of structural damage of the heart muscle, regardless of the underlying cardiac disorder.

"Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

"Congestive heart failure" is a progressive pathologic state where the heart is increasingly unable to supply adequate cardiac output (the volume of blood pumped by the heart over time) to deliver the oxygenated blood to peripheral tissues. As congestive heart failure progresses, structural and hemodynamic damages occur. While these damages have a variety of manifestations, one characteristic symptom is ventricular hypertrophy. Congestive heart failure is a common end result of a number of various cardiac disorders.

"Myocardial infarction" generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As a result of the increased stress or strain placed on the heart in prolonged hypertension due, for example, to the increased total peripheral resistance, cardiac hypertrophy has long been associated with "hypertension". A characteristic of the ventricle that becomes hypertrophic as a result of chronic pressure overload is an impaired diastolic performance. Fouad et al., *J. Am. Coll. Cardiol.* 4, 1500–6 (1984); Smith et al., *J. Am. Coll. Cardiol.* 5, 869–74 (1985). A prolonged left ventricular relaxation has been detected in early essential hypertension, in spite of normal or supranormal systolic function. Hartford et al., *Hypertension* 6, 329–338 (1984). However, there is no close parallelism between blood pressure levels and cardiac hypertrophy. Although improvement in left ventricular function in response to antihypertensive therapy has been reported in humans, patients variously treated with a diuretic (hydrochlorothiazide), a β-blocker (propranolol), or a calcium channel blocker (diltiazem), have shown reversal of left ventricular mass, without improvement in diastolic function. Inouye et al., *Am. J. Cardiol.* 53, 1583–7 (1984).

Another complex cardiac disease associated with cardiac hypertrophy is "hypertrophic cardiomyopathy". This condition is characterized by a great diversity of morphologic, functional, and clinical features (Maron et al., *N. Engl. J. Med.* 316, 780–9 [1987]; Spirito et al., *N. Engl. J. Med.* 320, 749–55 [1989]; Louie and Edwards, *Prog. Cardiovasc. Dis.* 36, 275–308 [1994]; Wigle et al., *Circulation* 92, 1680–92 [1995]), the heterogeneity of which is accentuated by the fact that it afflicts patients of all ages (Spirito et al., *N. Engl. J. Med.* 336, 775–785 [1997]). The causative factors of hypertrophic cardiomyopathy are also diverse and little understood. Recent data suggest that β-myosin heavy chain mutations may account for approximately 30 to 40 percent of cases of familial hypertrophic cardiomyopathy (Watkins et al., *N. Engl. J. Med.* 326, 1108–14 [1992] Schwartz et al., *Circulation* 91, 532–40 [1995]; Marian and Roberts. *Circulation* 92, 1336–47 [1995]; Thierfelder et al., *Cell* 77, 701–12 [1994]; Watkins et al., *Nat. Gen.* 11, 434–7 [1995]).

Supravalvular "aortic stenosis" is an inherited vascular disorder, that is characterized by narrowing of the ascending aorta, but other arteries, including the pulmonary arteries, may also be affected. Untreated aortic stenosis may lead to increased intracardiac pressure resulting in myocardial hypertrophy and eventually heart failure and death. The pathogenesis of this disorder is not fully understood, but hypertrophy and possibly hyperplasia of medial smooth muscle are prominent features of this disorder. It has been reported that molecular variants of the elastin gene are involved in the development and pathogenesis of aortic stenosis. (U.S. Pat. No. 5,650,282 issued Jul. 22, 1997.)

"Valvular regurgitation" occurs as a result of heart diseases resulting in disorders of the cardiac valves. Various diseases, like rheumatic fever, can cause the shrinking or pulling apart of the valve orifice, while other diseases may result in endocarditis, an inflammation of the endocardium or lining membrane of the atrioventricular orifices and operation of the heart. Defects such as the narrowing of the valve stenosis or the defective closing of the valve result in an accumulation of blood in the heart cavity or regurgitation of blood past the valve. If uncorrected, prolonged valvular stenosis or insufficiency may result in cardiac hypertrophy and associated damage to the heart muscle, which may eventually necessitate valve replacement.

The treatment of all these, and other cardiac disorders accompanied by cardiac hypertrophy is subject of the present invention.

"Treatment" refers to both therapeutic treatment and prophylactic or preventative measures, wherein the object is to prevent or slow down (lessen) hypertrophy. Those in need of treatment include those already with the disorder as well as those prone to have the disorder or those in whom the disorder is to be prevented. The hypertrophy may result from any cause, including idiopathic, cardiotrophic, or myotrophic causes, or ischemia or ischemic insults, such as myocardial infarction.

"Chronic" administration refers to administration of the agent(s) in a continuous mode as opposed to an acute mode, so as to maintain the initial antihypertrophic effect for an extended period of time.

"Mammal" for purposes of treatment refers to any animal classified as a mammal, including humans, domestic and farm animals, and zoo, sports, or pet animals, such as dogs, cats, cows, horses, sheep, pigs, etc. Preferably, the mammal is human.

Administration "in combination with" one or more further therapeutic agents includes simultaneous (concurrent) and consecutive administration in any order.

B. Modes of Carrying out the Invention

1. Cardiac Hypertrophy Assays

In Vitro Assays a. Induction of Spreading of Adult Rat Cardiac Myocytes

In this assay, ventricular myocytes are isolated from a single (male Sprague-Dawley) rat, essentially following a modification of the procedure described in detail by Piper et al., "Adult ventricular rat heart muscle cells." In: *Cell Culture Techniques in Heart and Vessel Research*, H. M. Piper, ed., Berlin: Spinger-Verlag, 1990, pp. 36–60. This procedure permits the isolation of adult ventricular myocytes and the long-term culture of these cells in the rod-shaped phenotype. Phenylephrine and Prostaglandin $F_{2\alpha}$, ($PGF_{2\alpha}$) have been shown to induce a spreading response in these adult cells. Piper et al., supra; Lai et al., *Am J. Physiol.* 1996; 271 (*Heart Circ. Phvsiol.* 40):H2197–H2208. The inhibition of myocyte spreading induced by $PGF_{2\alpha}$, or $PGF_{2\alpha}$ analogs, (e.g. fluprostenol) and phenylephrine by various potential inhibitors of cardiac hypertrophy is then tested. A detailed protocol is described in the examples that follow.

In Vivo Assays a. Inhibition of Cardiac Hypertrophy Induced by Fluprostenol In Vivo This pharmacological model tests the ability of IFN-γ to inhibit cardiac hypertrophy induced in rats (e.g. male Wistar or Sprague-Dawley) by subcutaneous injection of fluprostenol (an agonist analog of $PGF_{2\alpha}$). It is known that rats with pathologic cardiac hypertrophy induced by myocardial infarction have chronically elevated levels of extractable $PGF_{2\alpha}$ in their myocardium. Lai et al, *Am. J. Physiol.* (*Heart Circ. Physiol.*) 271:H2197–H2208 (1996). Accordingly, factors that can inhibit the effects of fluprostenol on myocardial growth in vivo are potentially useful for treating cardiac hypertrophy. The effects of IFN-γ on cardiac hypertrophy are determined by measuring the weight of heart, ventricles, and left ventricle (normalized by body weight) relative to fluprostenol-treated rats not receiving IFN-γ. A detailed description of this assay is provided in the examples.

b. Pressure-Overload Cardiac Hypertrophy Assay.

For in vivo testing it is common to induce pressure-overload cardiac hypertrophy by constriction of the abdominal aorta of test animals. In a typical protocol rats (e.g. male Wistar or Sprague-Dawley) are treated under anesthesia, and the abdominal aorta of each rat is narrowed down just below the diaphragm. Beznak M., *Can. J. Biochem. Physiol.* 33, 985–94 (1955). The aorta is exposed through a surgical incision, and a blunted needle is placed next to the vessel. The aorta is constricted with a ligature of wool thread around the needle, which is immediately removed and which reduces the lumen of the aorta to the diameter of the needle. This approach is described, for example, in Rossi et al., *Am. Heart J.* 124, 700–709 (1992) and O'Rourke and Reibel, *P.S.E.M.B.* 200, 95–100 (1992). A detailed description of the protocol used by the present inventors is disclosed in the examples hereinbelow.

b. Effect on Cardiac Hypertrophy Following Experimentally Induced Myocardial Infarction (MI).

Acute MI is induced in rats by left coronary artery ligation and confirmed by electrocardiographic examination. A sham-operated group of animals is also prepared as control animals. Earlier data have shown that cardiac hypertrophy is present in the group of animals with MI, as evidenced by an 18% increase in heart weight-to-body weight ratio. Lai et al., supra. Treatment of these animals with candidate blockers of cardiac hypertrophy, e.g. IFN-γ provides valuable information about the therapeutic potential of the candidates tested.

2. Uses, Therapeutic Compositions and Administration of IFN-γ

In accordance with the present invention, IFN-γ can be used for the treatment of cardiac hypertrophy, i.e. the enlargement of heart, regardless of the etiology and pathogenesis. When an excessive pressure or volume load is imposed on the heart (ventricle), cardiac (myocardial) hypertrophy develops, providing a fundamental compensatory mechanism that permits the ventricle to sustain its burden. Krayenbuehl et al., *Eur. Heart J.* 4 (Suppl. A), 29 (1983). The character of the stress (increased preload, increased afterload, loss of myocytes, as in myocardial infarction, or primary depression of contractility) responsible of the development of hypertrophy plays a critical role in determining the nature of the hypertrophic response. Scheuer and Buttrick, *Circulation* 75(Suppl. I), 63 (1987). The present invention concerns the treatment of cardiac hypertrophy associated with any underlying pathological condition, including, without limitation, post myocardial infarction, hypertension; aortic stenosis, cardiomyopathy, valvular regurgitation, cardiac shunt, and congestive heart failure. The main characteristics of these conditions have been discussed hereinabove.

Particularly important is the use of IFN-γ for the prevention of cardiac failure following myocardial infarction. About 750,000 patients suffer from acute myocardial infarction (AMI) annually, and approximately one-fourth of all death in the United States are due to AMI. In recent years, thrombolytic agents, e.g. streptokinase, urokinase, and in particular tissue plasminogen activator (t-PA) have significantly increased the survival of patients who suffered myocardial infarction. When administered as a continuous intravenous infusion over 1.5 to 4 hours, t-PA produces coronary patency at 90 minutes in 69% to 90% of the treated patients. Topol et al., *Am. J. Cardiol.* 61, 723–8 (1988); Neuhaus et al., *J. Am. Coll. Cardiol.* 12, 581–7 (1988); Neuhaus et al., *J. Am. Col. Cardiol.* 14, 1566–9 (1989). The highest patency rates have been reported with high dose or accelerated dosing regimens. Topol, *J. Am. Coll. Cardiol.* 15, 922–4 (1990). t-PA may also be administered as a single bolus, although due to its relatively short half-life, it is better suited for infusion therapy. Tebbe et al., *Am. J. Cardiol.* 64 448–53 (1989). A t-PA variant, specifically designed to have longer half-life and very high fibrin specificity, TNK t-PA (a T103N,N 117Q, KHRR(296–299)AAAA t-PA variant, Keyt et al., *Proc. Natl. Acad. Sci. USA* 91, 3670–3674 (1994)) is particularly suitable for bolus administration. However, despite all these advances, the long-term prognosis of patient survival depends greatly on the post-infarction monitoring and treatment of the patients, which should include monitoring and treatment of cardiac hypertrophy.

Another important therapeutic indication is the treatment of cardiac hypertrophy associated with hypertension. As noted before, sustained hypertension is known to result in cardiac hypertrophy. Although certain hypotensive agents have been shown to reduce left ventricular mass, treatment does not always resulted in the improvement of diastolic function. Accordingly, IFN-γ can be administered in combination with β-adrenergic receptor blocking agents, e.g., propranolol, timolol, tertalolol, carteolol, nadolol, betaxolol, penbutolol, acetobutolol, atenolol, metoprolol, carvedilol: angiotensin converting enzyme (ACE) inhibitors, e.g., quinapril, captopril, enalapril, ramipril, benazepril, fosinopril, lisinopril; diuretics, e.g. chorothiazide, hydrochlorothiazide, hydroflumethazide, methylchlothiazide, benzthiazide, dichlorphenamide, acetazolamide, indapamide; and/or calcium channel blockers, e.g., diltiazem, nifedipine, verapamil, nicardipine. Pharmaceutical compositions comprising the therapeutic agents identified here by their generic names are commercially available, and are to be administered following the manufacturers' instructions for dosage, administration, adverse effects, contraindications, etc. (See, e.g. Physicians' Desk Reference, Medical Economics Data Production Co. Montvale, N.J., 51th Edition, 1997.)

IFN-γ may also be administered prophylactically to patients with cardiac hypertrophy, to prevent the progression of the condition, and avoid sudden death, including death of asymptomatic patients. Such preventative therapy is particularly warranted in the case of patients diagnosed with massive left ventricular cardiac hypertrophy (a maximal wall thickness of 35 mm or more in adults, or a comparable value in children), or in instances when the hemodynamic burden on the heart is particularly strong.

IFN-γ may also be useful in the management of atrial fibrillation, which develops in a substantial portion of patients diagnosed with hypertrophic cardiomyopathy.

IFN-γ is administered in the form of a pharmaceutical composition comprising IFN-γ as an active ingredient, in conjunction with a pharmaceutically acceptable carrier. Therapeutic formulations of IFN-γ for treating cardiac hypertrophy are prepared for storage by mixing IFN-γ having the desired degree of purity with optional physiologically acceptable carriers, excipients, or stabilizers (Remington's Pharmaceutical Sciences, supra), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics, or polyethylene glycol (PEG).

IFN-γ to be used for in vivo administration must be sterile. This is readily accomplished by filtration through sterile filtration membranes, prior to or following lyophilization and reconstitution. IFN-γ ordinarily will be stored in lyophilized form or in solution.

IFN-γ may be used in lyophilized form, in combination with other ingredients for reconstitution with an appropriate diluent at the time for use. Because IFN-γ is known to be acid labile, it has traditionally been handled at neutral or slightly alkaline pH. See, for example, U.S. Pat. No. 4,499,014 which discloses reactivation of a lyophilized acidic IFN-γ solution to a pH of 6 to 9. Neutral or slightly alkaline solutions of higher concentrations of IFN-γ are generally unsuitable as injectable formulations because of the immediate formation of a visible precipitate. Such precipitate may cause thrombosis on administration or decrease potency. European Patent Publication No. 0196,203 discloses reconstitution of lyophilized IFN-γ to a pH of 4 to 6.0.

Stable liquid pharmaceutical compositions comprising an effective amount of non-lyophilized IFN-γ along with a buffer capable of maintaining the pH at 4.0–6.0, a stabilizing agent, and a non-ionic detergent are disclosed in U.S. Pat. No. 5,151,265 issued 29 Sep. 1992. The stabilizing agent typically is a polyhydric sugar alcohol, such as mannitol, and the non-ionic detergent may be a surfactant, e.g. polysorbate 80 or polysorbate 20. The non-ionic detergent preferably is present in a range of about 0.07 to 0.2 mg/ml, and most preferably in a concentration of about 0.1 mg/ml. Suitable buffers are conventional buffers of organic acids and salt thereof, such as nitrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartarate buffers (e.g., tartaric acid-sodium tartarate mixture, tartaric acid-potassium tartarate mixture, tartaric acid-sodium hydroxide mixture, etc.), fumarate buffers (e.g. fumaric acid-monosodium fumarate mixture, fumaric acid-disodium fumarate mixture, monosodium fumarate-disodium fumarate mixture, etc.), gluconate buffers (e.g. gluconic acid-sodium gluconate mixture, gluconic acid-sodium hydroxide mixture, gluconic acid-potassium gluconate mixture, etc.), oxalate buffers (e.g., oxalic acid-sodium oxalate mixture, oxalic acid-sodium hydroxide mixture, oxalic acid-potassium oxalate mixture, etc.), lactate buffers (e.g. lactic acid-sodium lactate mixture, lactic acid-sodium hydroxide mixture, lactic acid-potassium lactate mixture, etc.), and acetate buffers (e.g., acetic acid-sodium acetate mixture, acetic acid-sodium hydroxide mixture, etc.)

A known commercial liquid formulation of IFN-γ (Actimmune® rhuIFN-γ-1b, Genentech, Inc.) is a sterile, clear, colorless unpreserved solution filled in a single-dose vial for subcutaneous injection. Each 0.5 ml vial of Actimmune contains 100 μg (3 million U, specific activity: 30 million U/mg) of IFN-γ-1b formulated in 20 mg mannitol, 0.36 mg sodium succinate, 0.05 mg polysorbate 20 and Sterile Water for Injection.

Preserved pharmaceutical compositions to be used in accordance with the present invention, which are suitable for repeated use, preferably contain:
 a) IFN-γ not subjected to prior lyophilization;
 b) an acetate buffer capable of maintaining the pH between about 4 and about 6 (the pH range of maximum stability of the protein in solution);
 c) a non-ionic detergent primarily to stabilize the protein against agitation-induced aggregation;
 d) an isotonifier;
 e) a preservative selected from the group of phenol, benzyl alcohol and a benzethonium halide, e.g. chloride; and
 f) water.

The non-ionic detergents (surfactants) may, for example, be polysorbates (e.g. polysorbate [Tween] 20, 80, etc.) or poloxamers (e.g. poloxamer 188). The use of non-ionic surfactants permits the formulation to be exposed to shear surface stresses without causing denaturation of the protein. Further, such surfactant containing formulations may be employed in aerosol devices such as those used in a pulmonary dosing, and needleless jet injector guns (see, e.g. EP 257,956).

The isotonifier is present to ensure isotonicity of the liquid compositions of the present invention, and includes polyhydric sugar alcohols, preferably trihydric or higher sugar alcohols, such as glycerin, erythritol, arabitol, xylitol, sorbitol and mannitol. These sugar alcohols can be used alone or in combination. Alternatively, sodium chloride or other appropriate inorganic salts may be used to render the solutions isotonic.

The acetate buffer may, for example, be an acetic acid-sodium acetate mixture, acetic acid-sodium hydroxide mixture, etc. The pH of the liquid formulation of this invention is buffered in the range of about 4.0 to 6.0, preferably 4.5 to 5.5, and most preferably at about pH 5.

The preservatives phenol, benzyl alcohol and benzethonium halides, e.g. chloride, are known antimicrobial agents.

In a preferred embodiment, IFN-γ is administered in the form of a liquid pharmaceutical composition which comprises the following components:

| | |
|---|---|
| IFN-γ | 0.1–2.0 mg/ml |
| sodium acetate (pH 5.0) | 5–100 mM |
| Tween 20 | 0.1 to 0.01% by weight |
| phenol | 0.05 to 0.4% by weight |
| mannitol | 5% by weight |
| water for injection, USP | up to 100%, | wherein the percentage amounts are based on the weight of the composition. Phenol can be replaced by 0.5–1.0% by weight of benzyl alcohol, and mannitol can be replaced by 0.9% by weight sodium chloride.

Most preferably, the compositions comprise

| | |
|---|---|
| IFN-γ | 0.1 to 1.0 mg/ml |
| sodium acetate (pH 5.0) | 10 mM |
| Tween 20 | 0.01% by weight |
| phenol | 0.2% |
| mannitol | 5% |

Phenol can be replaced by 0.75 by weight benzyl alcohol and mannitol by 0.9% by weight sodium chloride.

The preserved liquid formulations preferably contain multiple doses of a therapeutically effective amount of IFN-γ. In view of the narrow host range of this polypeptide, for the treatment of human patients liquid formulations comprising human IFN-γ, more preferably native sequence human IFN-γ, are preferred. As a biological response modifier, IFN-γ exerts a wide variety of activities on a wide range of cell types, in a variety of human and non-human mammalian species. The therapeutically effective dose will, of course, vary depending on such factors as the pathological condition to be treated (including prevention), the patient's age, weight, general medical condition, medical history, etc., and its determination is well within the skill of a practicing physician. The effective dose generally is within the range of from about 0.001 to about 1.0 mg/kg, more preferably about 0.01–1 mg/kg, most preferably about 0.01–0.1 mg/kg. In such formulations huIFN-γ will preferably exhibit a specific activity of on the order of about $2 \times 10^7$ U/mg of protein or greater when tested on A549 cells against encephalomyocarditis virus. It should be appreciated that endotoxin contamination should be kept minimally at a safe level, for example, less than 0.5 ng/mg protein. Moreover, for human administration, the liquid formulations should meet sterility, pyrogenicity, general safety, and purity as required by FDA Office and Biologics standards.

The route of IFN-γ administration is in accord with known methods, e.g., injection or infusion by intravenous, intraperitoneal, intracerebral, intramuscular, intraocular, intraarterial, or intralesional routes, or by sustained-release systems as noted below. Therapeutic IFN-γ compositions generally are placed into a container having a sterile access port, for example, an intravenous solution bag or vial having a stopper pierceable by a hypodermic injection needle. The formulations are preferably administered as repeated intravenous (i.v.), subcutaneous (s.c.) or intramuscular (i.m.) injections, or as aerosol formulations suitable for intranasal or intrapulmonary delivery (for intrapulmonary delivery see, e.g. EP 257,956).

The stable aqueous compositions of IFN-γ are preferably contained in vials, containing up to about 30 therapeutically effective doses of IFN-γ. The bioactivity of IFN-γ preferably remains within about 20% from the bioactivity exhibited at the time of first administration for at least about 14 days, more preferably for at least about 200 days following first administration.

IFN-γ can also be administered in the form of sustained-released preparations. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167–277 [1981] and Langer, *Chem. Tech.* 12: 98–105 [1982] or poly(vinylalcohol)), polylactides (U.S. Pat. No. 3,773,919, EP 58,481), copolymers of L-glutamic acid and gamma ethyl-L-glutamate (Sidman et al., Biopolymers, 22: 547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release IFN-γ compositions also include liposomally entrapped IFN-γ. Liposomes containing IFN-γ are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal therapy.

An effective amount of IFN-γ to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. The recommended dosage for the administration of IFN-γ (Actimmune®, Genentech, Inc.) to treat patients with chronic granulomatous disease is 50 mcg/m² (1.5 million U/m²) for patients whose body surface area is greater than 0.5 m², and 1.5 mcg/kg/dose for patients whose body surface area is equal to or less than 0.5 m², administered as a subcutaneous injection, three times a week. This is valuable guidance for a physician to determine the optimal effective dose for the treatment of cardiac hypertrophy. The clinician will administer IFN-γ until a dosage is reached that achieves the desired effect for treatment of the heart dysfunction. For example, if the objective is the treatment of congestive heart failure, the amount would be one which inhibits the progressive cardiac hypertrophy associated with this condition. The progress of this therapy is easily monitored by echo cardiography. Similarly, in patients with hypertrophic cardiomyopathy, IFN-γ can be administered on an empirical basis, relying on the patient's subjective perception of benefit.

IFN-γ may be administered in combination with other therapeutic agents used for the treatment (including prevention) of cardiac hypertrophy. For example, IFN-γ therapy can be combined with the administration of inhibitors of known cardiac myocyte hypertrophy factors, e.g. inhibitors of α-adrenergic agonists, e.g. phenylephrine; endothelin-1; CT-1; LIF; angiotensin converting enzyme; and angiotensin II. Inhibitors of cardiac hypertrophy factor (CHF, cardiotrophin or cardiotrophin-1, see, e.g. U.S. Pat. No. 5,679,545) are particularly preferred for combination therapy.

Preferred candidates for combination therapy in the treatment of hypertrophic cardiomyopathy are adrenergic-blocking drugs (e.g., propranolol, timolol, tertalolol, carteolol, nadolol, betaxolol, penbutolol, acetobutolol, atenolol, metoprolol, carvedilol), verapamil, difedipine, diltiazem. Treatment of hypertrophy associated with high blood pressure may require the use of antihypertensive drug therapy, using calcium channel blockers, e.g. diltiazem, nifedipine, verapamil, nicardipine; β-adrenergic blocking agents; diuretics, e.g., chorothiazide, hydrochlorothiazide, hydroflumethazide, methylchlothiazide, benzthiazide, dichlorphenamide, acetazolamide, indapamide; and/or ACE-inhibitors, e.g., quinapril, captopril, enalapril, ramipril, benazepril, fosinopril, lisinopril.

The effective amount of the therapeutic agents administered in combination with IFN-γ will be at the physician's or veterinarian's discretion. Dosage administration and adjustment is done to achieve optimal management of the conditions to be treated, and ideally takes into account use of diuretics or digitalis, and conditions such as hyper- or hypotension, renal impairment, etc. The dose will additionally depend on such factors as the type of the therapeutic agent to be used and the specific patient being treated. Typically, the amount employed will be the same dose as that used, if the given therapeutic agent is administered without IFN-γ.

EXAMPLES

Example 1

Inhibition of $PGF_{2\alpha}$-Induced Spreading Response of Adult Myocytes by IFN-γ

Materials and Methods

Adult myocyte cultures The procedure used for the isolation of ventricular myocytes from adult rats was a modification of a procedure described by Piper et al., supra, and is detailed in Lai et al., supra. For each myocyte preparation, one male Sprague-Dawley rat weighing about 250 g was anesthetized with pentobarbital sodium, and the heart was removed. Extraneous tissue was trimmed from the heart, and it was mounted onto a Langendorff system that was temperature controlled at 37° C. The heart was perfused with about 40 ml of Krebs buffer (110 mM NaCl, 2.6 mM KCl, 1.2 mM $KH_2PO_4$, 1.2 mM $MgSO_4.7H_2O$, 25 mM $NaHCO_3$ and 11 mM glucose). A solution containing 30 mg of collagenase and 12.5 μl of 100 mM $CaCl_2$ in 50 ml of Krebs buffer was then recirculated through the heart for 30 minutes. The heart was removed from the Langendorff apparatus, and the atria and connective tissues were removed. The ventricles were cut into 2 mm cubes with dissecting scissors, and further digested in a fresh collagenase solution (30 mg collagenase and 400 mg BSA dissolved in Krebs buffer with 12.5 μl of 100 mM $CaCl_2$) for five minutes at 37° C. During the digestion, the tissue suspension was gently band shaken one time per minute. After the digestion, the supernatant was removed and saved, and the remaining tissue was further digested in fresh collagenase solution for an additional five minutes.

Isolated adult rat myocytes were plated on laminin-coated plates at a density of $3 \times 10^3$ cells/ml. After 72 hours of appropriate stimulation, the cells were fixed with gluteraldehyde and stained with Eosin Y. Images of rod shaped cells were captured under fluorescent microscopy and maximum breadth was determined using imaging software (Simple 32, Compix Imaging, Mars, Pa.).

Results

IFN-γ Inhibits the Spreading of Adult Cardiac Myocyte Induced by the Hypertrophy Factors $PGF_{2\alpha}$ and Phenylephrine.

$PGF_{2\alpha}$, and the α-adrenergic agonist phenylephrine have been shown to induce hypertrophy of cultured neonatal rat cardiac myocytes (Adams et al., *J. Biol. Chem.* 271: 1179–1186 [1996]; Lai et al., *Am. J. Physiol.(Heart Circ. Physiol.)* 271:H2197–H2208 [1996];Meidell et al., *Am. J. Physiol.* 251:H1076–H1084 [1986]; Simpson, J. Clin. Invest. 72:732–738 [1983]; Simpson, *Circ. Res.* 56:884–894 [1985]). Adult rat ventricular myocytes spread when exposed to these factors in culture (Lai et al., supra; Piper et al., "Adult ventricular rat heart muscle cells", in: *Cell Culture Techniques in Heart and Vessel Research*, H. M. Piper, Editor, 1990, Springer-Verlag: Berlin, p. 36–60.) Adult myocytes have a rod-like morphology. When these cells are exposed to 0.1 μM $PGF_{2\alpha}$, the rod shaped cells flatten and spread (FIG. 1). The spreading response was quantified by measuring the maximum cell breadth of at least 200 rod shaped cells and plotting this value vs the percent frequency of cell breadth in the population. $PGF_{2\alpha}$ induced a significant change in the maximum cell breadth as evidenced by a shift in the population distribution for this parameter compared to control cells (P<0.001). Treating cells with IFN-γ significantly inhibited their response to $PGF_{2\alpha}$ (P<0.001 $PGF_{2\alpha}$+IFN-γ compared to $PGF_{2\alpha}$). The inhibitor effect of IFN-γ on $PGF_{2\alpha}$-induced myocyte spreading was dose dependent (FIG. 2) over a concentration range that is consistent with the biological response to IFN-γ in cardiac myocytes and other cell systems (Singh et al, *J. Biol. Chem.* 271: 1111–1117 [1996]; Pinsky et al., *J. Clin. Invest.* 95:766–685 [1995]; Ungureanu-Longrois et al., *Circ. Res.* 77:494–502 [1995]; Soderberg-Naucler et al., *J. Clin. Invest.* 100:3154–3163 [1997]; Gou et al., *J. Clin. Invest.* 100: 829–838 [1997]; Marra et al., *Can J. Cardiol.* 12:1259–1267 [1996]). The ability to inhibit $PGF_{2\alpha}$, induced myocyte spreading appears to be specific to IFN-γ since several other cytokines including IL-1α, IL-1β, IL-2, IL-6, TNF-α, IFN-α, and IFN-β could not inhibit the spreading response. The inhibitory effect of IFN-γ is not specific for $PGF_{2\alpha}$. IFN-γ can also inhibit spreading induced by phenylephrine (FIG. 3).

Example 2

Inhibition of Cardiac Hypertrophy In Vivo

Materials and Methods

Animals All experimental procedures conformed to the guiding principles of the American Physiology Society, and were approved by Genentech's Institutional Animal Care and Use Committee. The animals used in this study were male Sprague/Dawley (SD) rats (8 weeks of age, Charles River Breeding Laboratories, Inc.). The animals were acclimated to the facility for at least one week before experiments, fed a pelleted rat chow and water ad libitum, and housed in a light and temperature controlled room.

Administration of fluprostenol and/or IFN-γ Rats received subcutaneous injection of fluprostenol (Cayman Chemical, Ann Arbor, Mich.) at 0.15 mg/kg, recombinant mouse IFN-γ (Genentech, Inc., South San Francisco, Calif.) at 0.08 mg/kg, combination of fluprostenol and IFN-γ, or saline vehicle, twice a day for 14 days. In the IFN-γ and fluprostenol+IFN-γ groups, animals were pretreated with IFN-γ for one day. Body weight was measured before and after treatment. A previous study has shown that the dose of fluprostenol used here is the lowest dose which produces a significant cardiac hypertrophy in rats. Lai et al., supra. A pilot study demonstrated that IFN-γ at the dose indicated above inhibited fluprostenol-induced cardiac hypertrophy with little effects on body weight in rats.

Hemodynamic assessment Thirteen days after treatment, rats were anesthetized with intraperitoneal injection of ketamine 80 mg/kg (Aveco Co., Inc., Fort Dodge, Iowa) and xylazine 10 mg/kg (Rugby Laboratories, Inc., Rockville Center, N.Y.). A catheter (PE-10 fused with PE 50) filled with heparin-saline solution (50 U/ml) was implanted into the abdominal aorta, via the right femoral artery, for measurement of mean arterial pressure (MAP) and heart rate (HR). The catheter was exteriorized and fixed at the back of the neck.

One day after catheterization, the arterial catheter was connected to a Model CP 10 pressure transducer (Century Technology Company, Inglewood, Calif., USA) that was coupled to a Grass Model 7 polygraph (Grass Instruments, Quincy, Mass., USA). MAP and HR were measured simultaneously in conscious, unrestrained rats.

Measurement of organ weights Under anesthesia with ketamine/xylazine, the heart, kidney, and spleen were removed, dissected and weighed. The left ventricle was stored at 80° C. for evaluation of gene expression.

Animal model of pressure overload The induction of pressure overload by partial ligation of the abdominal aorta in rats was as described previously. Kimura et al., *Am. J. Physiol.* 1989:256 (*Heart Circ. Physiol.* 25):H1006–H1-11; Batra et al., *J. Cardiovasc. Pharmacol.* 17(suppl. 2), S151–S153 (1991). In brief, rats were anesthesized with ketamine/xylazine as described above. A 3 cm midline incision was made in the abdominal wall. The abdominal aorta between the diaphragm and the renal artery was exposed and looped with 5–0 silk suture. The suture was tightened around a gauge 23 needle, and then the needle was withdrawn. Sham animals received the surgery without tightening the suture.

Experimental protocol in rats with pressure overload The rats with aortic banding randomly received subcutaneous injection of IFN-γ at 0.08 mg/k twice a day for one day before surgery and for 14 days after surgery. Sham animals were not treated. Thirteen days after treatment, a catheter was implanted into the right carotid artery under anesthesia as indicated above. One day after implantation, arterial pressure and HR were measured in conscious rats. The heart and other organs including the liver, kidney, and spleen were removed, weighed, and fixed in 10% buffered formalin for pathological studies. The left ventricle was quickly dissected and frozen with liquid nitrogen in some animals and stored at −80° C. for assessment of gene expression.

Statistical analyisis Results are expressed as mean±SEM. One way analysis of variance (ANOVA) was performed to assess differences in parameters between groups. Significant differences were then subjected to post hoc analysis using Newman-Keuls method; $P<0.05$ was considered significant.

RNA preparation Total RNA was isolated using RNeasy Maxi Columns (Qïägen) according to the manufacturer's instructions.

RT-PCR Real-time RT-PCR (TaqMan) technology was used to compare the gene expression between the various treatment groups. An oligonucleotide probe containing a fluorescent reporter dye, 6-carboxytetramethyl-rhodamine (TAMRA), at the 3'-end was designed to hybridize to the amplicon defined by two PCR primers. A 3'-blocking phosphate prevents extension of the probe. The reporter dye is released from the probe by the 5' exonuclease activity of Taq polymerase during the extension phase of PCR reaction. The resulting fluorescence is monitored in the reaction tube by the sequence detector and quantified without further manipulation, hence the term "real-time". The threshold cycle number (Ct), defined as the point where the reporter fluorescence reaches a value greater than 10 times the standard deviation of the baseline, is proportional to the amount of amplicon produced from the sample. Since the fluorescence is detected during the exponential phase of the amplification, none of the reaction components are limiting. In each experiment, a control is analyzed that lacks the RNA template to monitor for contamination, and another control is included where the RT step is omitted to eliminate amplification of possible contaminating DNA as the source of the signal. Reactions are optimized to give the greatest fluorescence signal and smallest Ct by titration of magnesium and primer concentrations, and the product is run on an agarose gel to verify the presence of a single band at the predicted molecular weight. In addition, the sequence of the amplicon is screened against Genbank to eliminate the possibility of overlap with closely related genes.

For each sample the mRNA for each target gene is determined using a standard curve as described below and then normalized to the amount of glyceraldehyde-3-phosphate-dehydrogenase (GAPDH) in the sample (see below for specifics of this calculation). The relative abundance of each target gene to GAPDH can then be compared among treatment groups.

RT-PCR was performed on 1 ng of total RNA per reaction using the TaqMan Model 7700 Sequence Detector (ABI-Perkin Elmer) (Gibson et al., *Genome Res.* 6, 995–1001 [1996]). Amplification reaction conditions (for 50 μl) were 1×TaqMan Buffer A, 200 μM dATP, dCTP, dGTP, and 400 μM dUTP, 10% glycerol, 6.5 mM $MgCl_2$, 50 U MuLV reverse transcriptase, 20 U RNase Inhibitor, 1.25 U Ampli-Taq Gold, 100 nM forward and reverse primers, and 100 nM fluorogenic probe. RT-PCR reagents and glycerol were purchased from Perkin Elmer and Sigma, respectively. Reactions were performed in MicoAmp Optical Tubes and Caps (ABI-Perkin Elmer). TaqMan primers and probes were designed according to guidelines determined by Perkin Elmer and synthesized at Genentech, Inc., except for those for rodent GAPDH which were a generous gift from Perkin Elmer. Reverse transcription was performed at 48° C. for 30 minutes followed by heat activation of AmpliTaq Gold at 95° C. for 10 minutes. Thermal cycling was at 95° C. for 30 seconds and 60° for 1.5 minutes for 40 cycles.

Quantitation of the TaqMan results was performed as described by Heid et al., *Genome Res.* 6:986–994 (1996), with modifications. Briefly, standard curves (1:5 serial dilution) for each target gene of interest were run in duplicate. The Ct was plotted on the Y axis vs the log of the total RNA concentration (X axis), and the equation describing the line was determined. MRNA for each target gene was determined from the appropriate standard curve by entering the Ct (Y value) and solving for the input mRNA (X). The value for the target gene was then normalized to GAPDH by solving the following equation: $10^{X1}/10^{X2}$, where X1 is the target gene, and X2 is GAPDH.

Results

IFN-γ Inhibits Cardiac Hypertrophy In Vivo

Figure 4A:
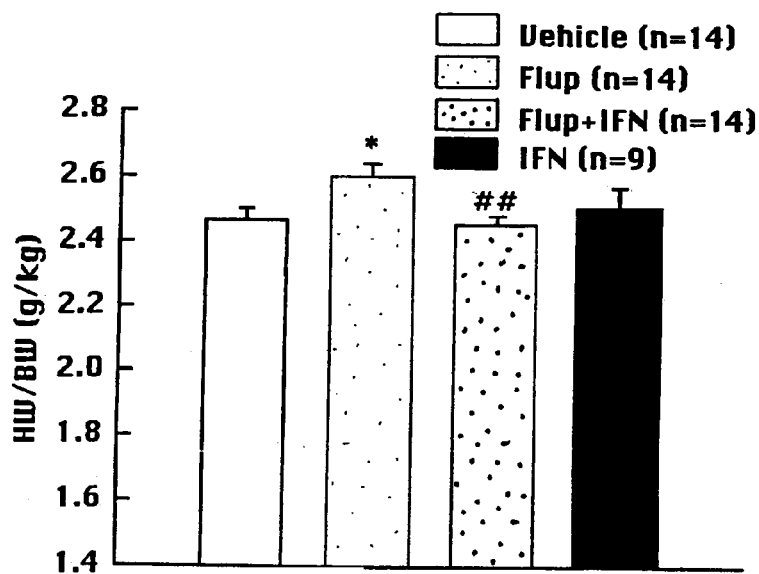
FIGS. 4A–4C Effects of IFN-γ on cardiac hypertrophy induced by fluprostenol in rats. Data are presented as mean±SEM. The number in parenthesis is the number of animals in each group. *P<0.05, *P<0.01, compared to the vehicle group. #P<0.05, ##P<0.01, compared to the Flup group. Flup: fluprostenol; IFN=IFN-γ; HW: heart weight; BW: body weight; VW: ventricular weight; LVW: left ventricular weight.
Figure 4B:
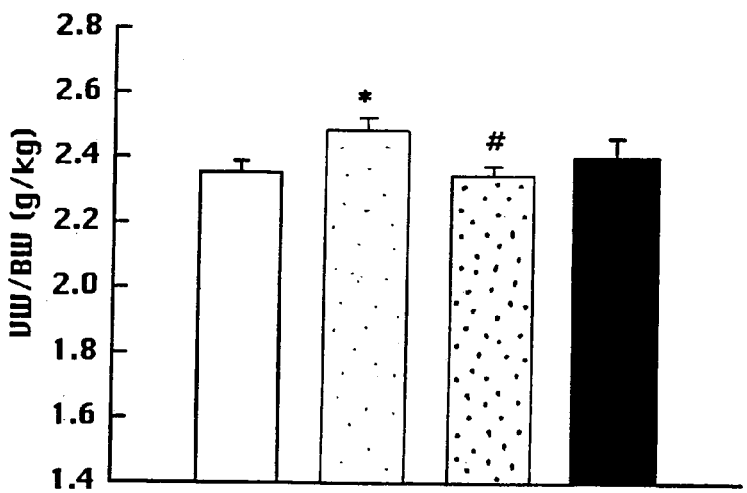
Figure 4C:
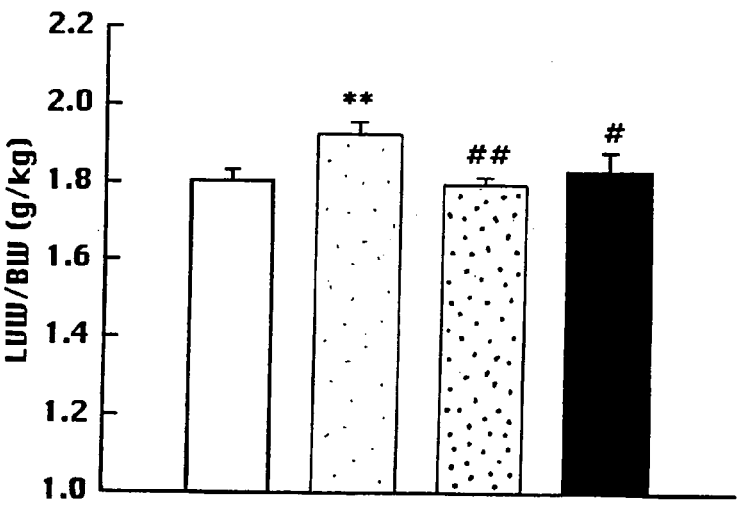

Chronic administration of fluprostenol, an agonist analog of $PGF_{2\alpha}$, has been shown to induce cardiac hypertrophy in vivo, and rats with pathologic cardiac hypertrophy induced by myocardial infarction have chronically elevated levels of extractable $PGF_{2\alpha}$ in their myocardium (Lai et al., supra). Thus, factors that can inhibit the effects of $PGF_{2\alpha}$ on myocardial growth in vivo may be useful for treating cardiac hypertrophy. Rats were dosed with fluprostenol in the presence and absence of IFN-γ for two weeks, and the effects on cardiac hypertrophy were determined. Absolute weight of the heart, ventricles, and left ventricle tended to increase in the fluprostenol-treated rats, compared to vehicle controls, and there was significant decrease in these parameters in rats treated with fluprostenol+ IFN-γ relative to fluprostenol treated rats (Table 1). Treatment with fluprostenol resulted in a significant increase in the ratio of heart, ventricular, and left ventricular weights to body weight (BW), indicating that fluprostenol induced cardiac hypertrophy (FIG. 4). IFN-γ inhibited fluprostenol induced hypertrophy. Rats receiving fluprostenol+IFN-γ had significantly decreased heart, ventricular and left ventricular weight, normalized by BW, compared to animals in the fluprostenol groups (FIG. 4). Comparison between the IFN-γ and vehicle treated groups showed that administration of IFN-γ alone did not significantly alter absolute or BW-normalized heat, ventricular, or left ventricular weights (Table 1, FIG. 4).

Figure 5A:
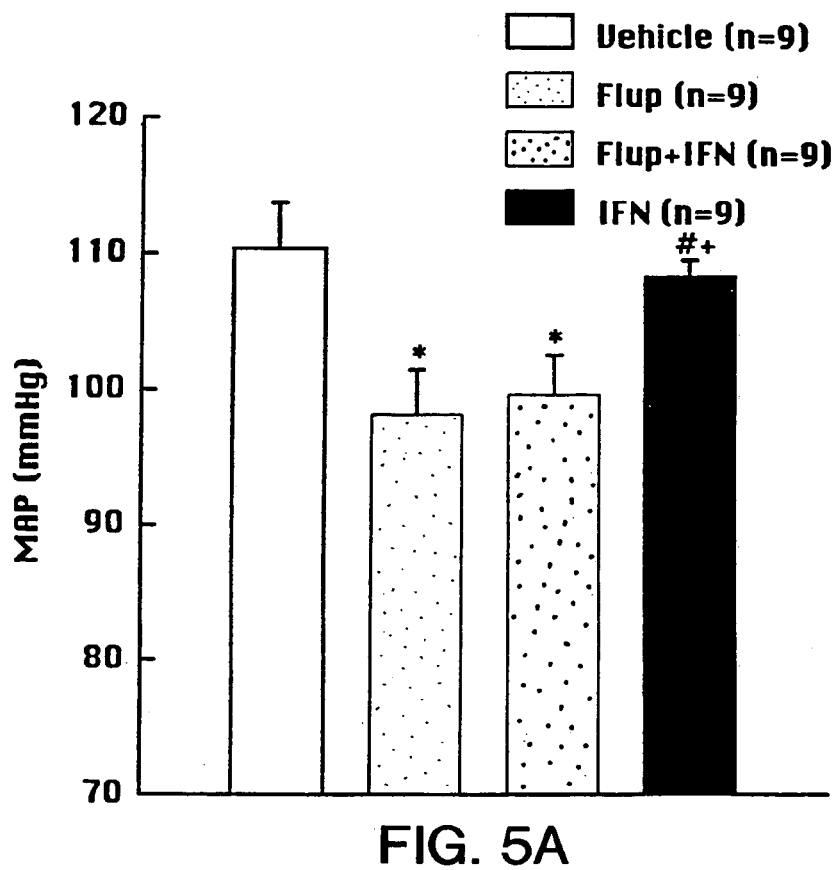
FIGS. 5A–5B Effects of Flup and/or IFN on MAP and HR. Data are presented as mean±SEM. The number in parenthesis is the number of animals in each group. *P<0.05, compared to the vehicle group. #P<0.05, compared to the Flup group. +P<0.05, compared to the Flup+IFN group. Flup: fluprostenol; IFN: IFN-γ; MAP: mean arterial pressure; HR: heart rate.
Figure 5B:
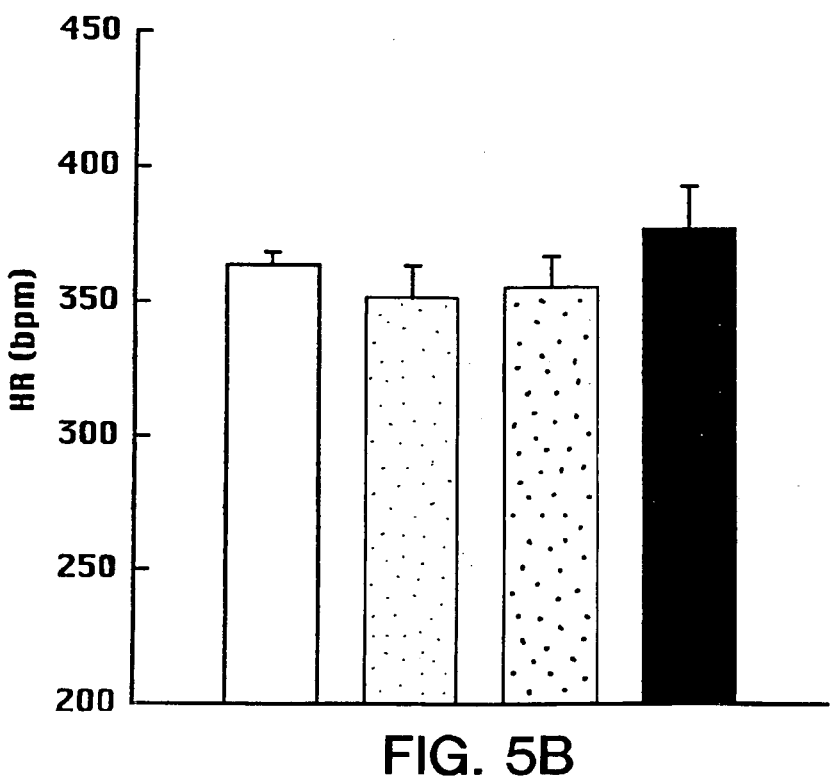

Chronic administration of fluprostenol was associated with a significant decline in mean arterial pressure (MAP) compared to vehicle treated controls (FIG. 5). IFN-γ had no effect on MAP compared to vehicle, and did not affect the MAP of animals treated with fluprostenol. There was significant alteration in the heart rate in the four treatment groups (FIG. 5). These results indicate that IFN-γ did not inhibit hypertrophy induced by fluprostenol by counteracting the hemodynamic effects of the treatment.

IFN-γ not only inhibited the increase in cardiac mass associated with fluprostenol administration, but also the alterations in cardiac gene expression associated with fluprostenol induced hypertrophy (FIG. 6). There was an increase in the abundance of mRNA for α-skeletal actin, collagen I, and natriuretic factor in the hearts of rats treated with fluprostenol compared to vehicle. The mRNA for sarcoplasmic reticulum calcium ATPase was significantly reduced in these rats. IFN-γ inhibited all but the atrial natriuretic factor response.

Figure 7A:
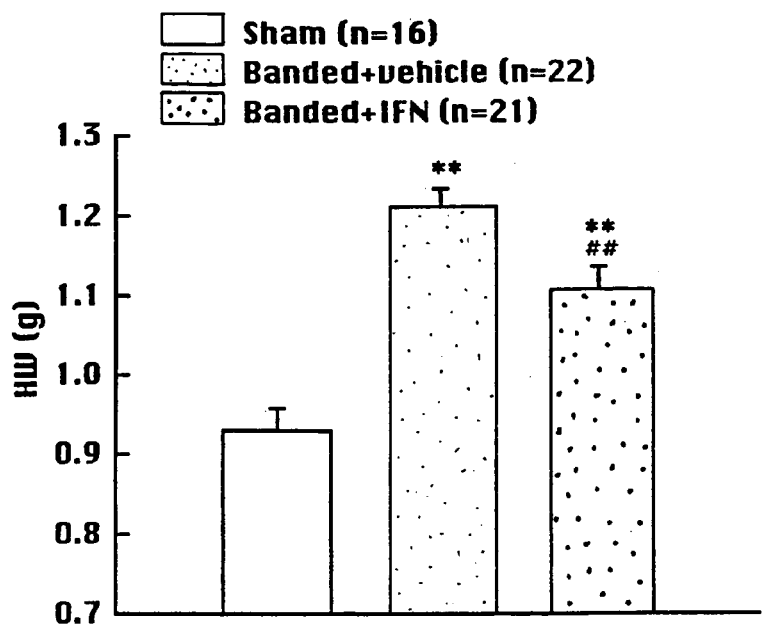
FIGS. 7A–7C Effects of IFN-γ on heart weight, ventricular weight, and left ventricular weight in rats with pressure overload. Data are presented as mean±SEM. The number in parenthesis is the number of animals in each group. **P<0.01, compared to the sham group. ##P<0.01, compared to the Banded+vehicle group. Sham: sham-operated rats; Banded: aortic-banded rats; IFN: IFN-γ; HW: heart weight; VW: ventricular weight: LVW: left ventricular weight.
Figure 7B:
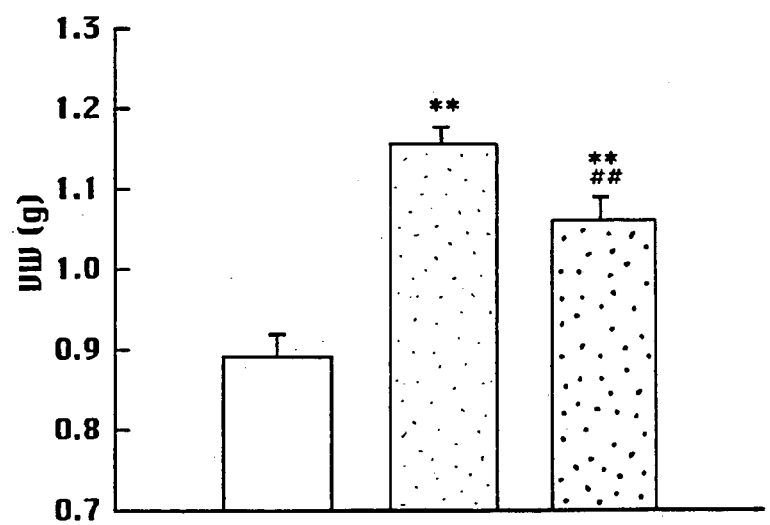
Figure 7C:
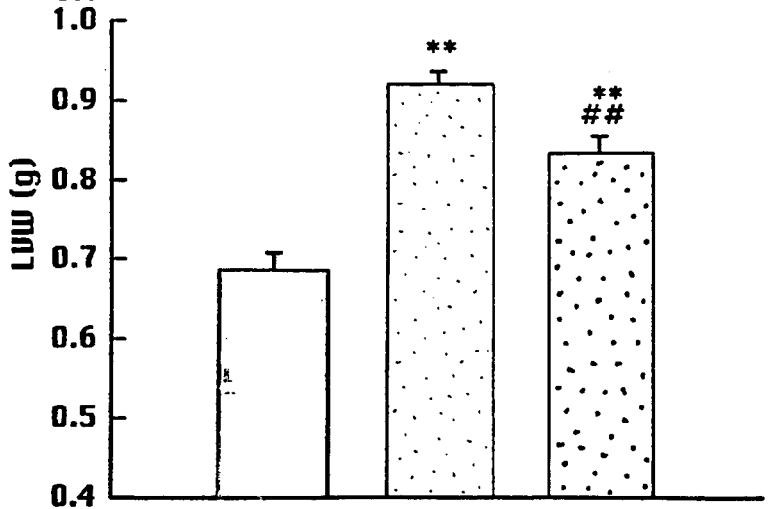
Figure 8A:
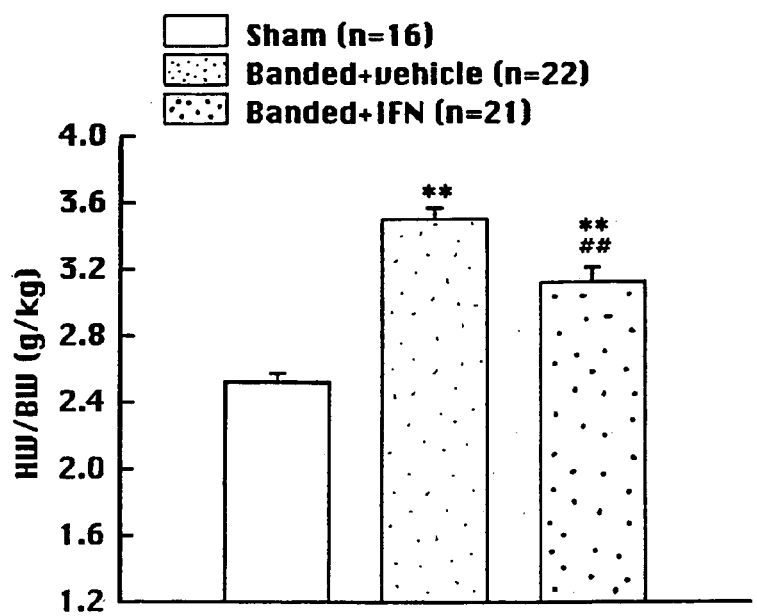
FIGS. 8A–8C Effects of IFN-γ on the ratio of heart weight, ventricular weight, and left ventricular weight to body weight in rats with pressure overload. Data are presented as mean±SEM. The number in parenthesis is the number of animals in each group. **P<0.01, compared to the sham group. ##P<0.01, compared to the Banded+vehicle group. Sham: sham-operated rats; Banded: aortic-banded rats: IFN: IFN-γ; HW: heart weight: BW: body weight; VW: ventricular weight; LVW: left ventricular weight.
Figure 8B:
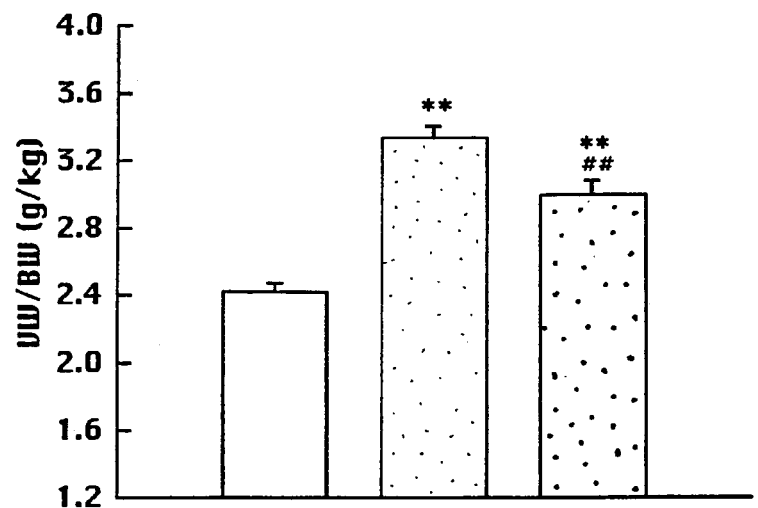
Figure 8C:
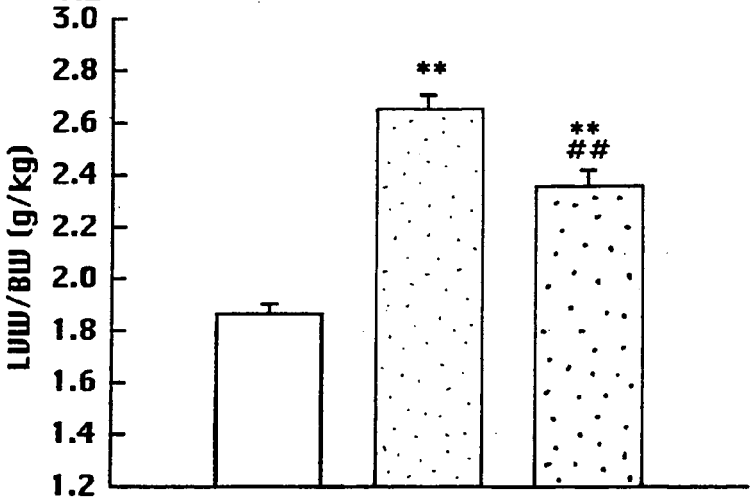

IFN-γ was also tested in a rodent model of cardiac hypertrophy induced by pressure overload generated by abdominal aortic banding. Aortic constriction resulted in cardiac hypertrophy as evidenced by substantial increases in absolute heart, atrial, ventricular and left ventricular weights, and also the ratios of these weights to BW. Treatment with IFN-γ significantly attenuated cardiac hypertrophy in this model (Table 2 and FIGS. 7 and 8).

The effect of IFN-γ on other organs was also examined (Table 2). Neither aortic banding nor IFN-γ treatment altered kidney weight and the ratio of kidney weight to BW. Compared to sham-operated animals, liver weight and the ratio of BW tended to decrease in aortic-banded rats treated with vehicle, but not in those treated with IFN-γ. Aortic constriction caused a significant elevation in absolute and BW-normalized spleen weight, that was exaggerated by IFN-γ treatment. Thus, the effects of IFN-γ on cardiac mass were not due to a generalized effect on organ weight.

Figure 9A:
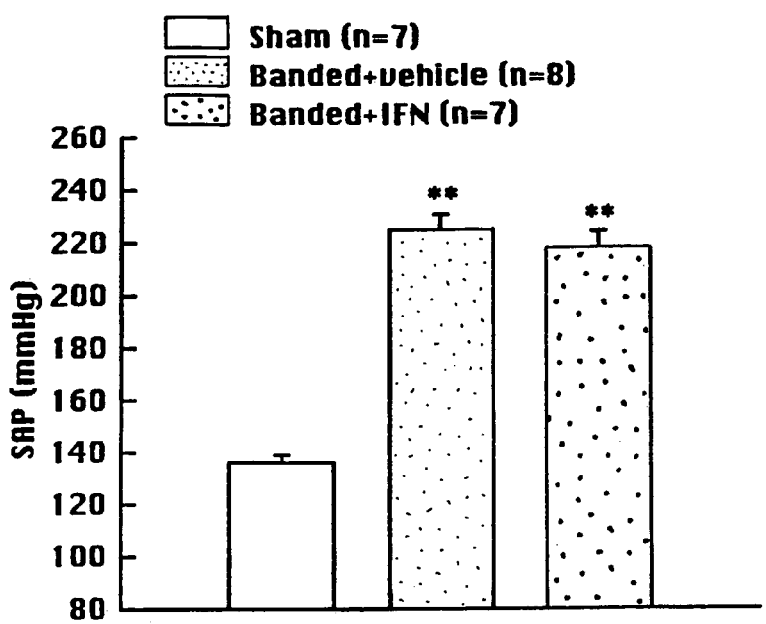
FIGS. 9A–9C Effects of IFN-γ on systolic arterial pressure, mean arterial pressure, and diastolic arterial pressure in rats with pressure overload. The number in parenthesis is the number of animals in each group. **P<0.01, compared to the sham group. Sham: sham-operated rats; Banded: aortic-banded rats; IFN: IFN-γ, SAP: systolic arterial pressure; MAP: mean arterial pressure; DAP: diastolic arterial pressure.
Figure 9B:
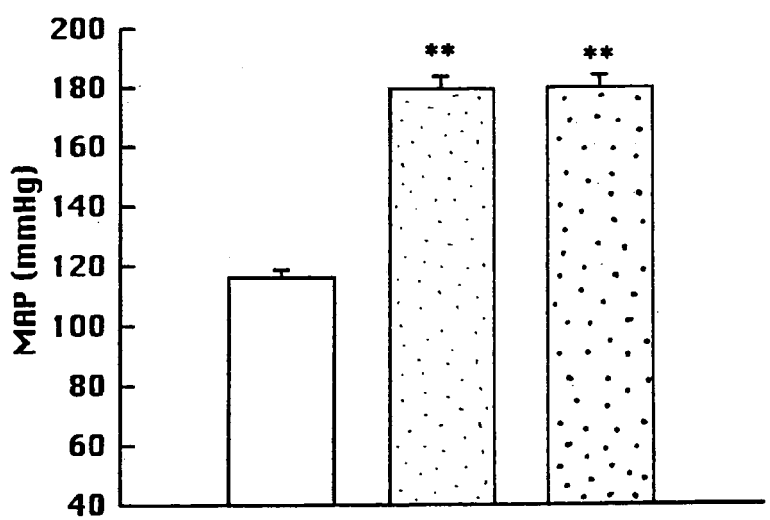
Figure 9C:
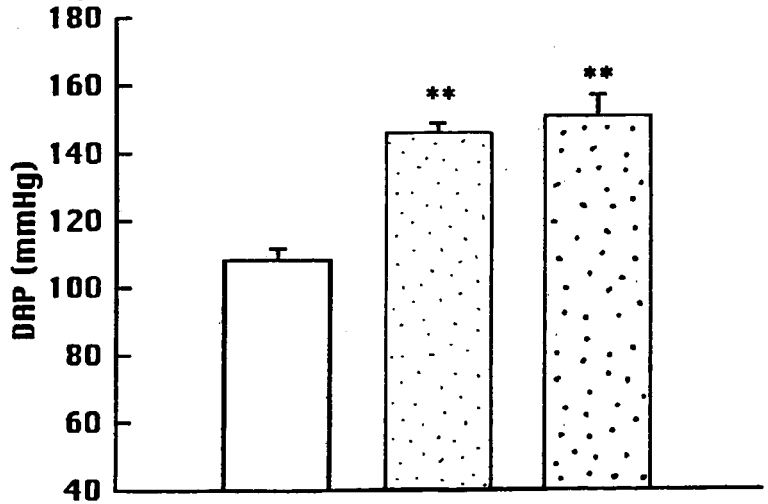

Mean arterial pressure, systolic pressure, and diastolic pressure were markedly higher in rats with aortic constriction compared to sham-operated controls, and the incremental increase in arterial pressure was not different between banded rats treated with IFN-γ or vehicle (FIG. 9). This result indicates that the attenuation of cardiac hypertrophy observed in banded rats receiving IFN-γ did not relate to an alteration in afterload.

Aortic constriction resulted in several changes in cardiac gene expression. The relative abundance of mRNA for β-myosin heavy chain, α-smooth muscle and α-skeletal actins, atrial natriuretic factor, collagens I and III, and fibronectin were all increased in banded rats compared to sham-operated controls. The effects on two of these genes; α-smooth muscle actin and collagen I were inhibited by IFN-γ (Table 3).

Taken together, the results in Examples 1 and 2 show that IFN-γ can inhibit cardia hypertrophy. The effects of IFN-γ are not limited to inhibiting an increase in cardiac mass induced by hypertrophic stimuli, IFN-γ can also inhibit certain of the molecular alterations that occur in the hypertrophied heart at the level of gene expression. It is especially noteworthy that IFN-γ inhibited the induction of collagen I gene expression in vivo, both in response to chronic stimulation with fluprostenol and in a model of hypertrophy induced by pressure overload. Collagen I accounts for approximately 75% of myocardial collagen (Ju et al., Can. J. Caridol. 12:1259–1267 [1996]). Increased extracellular matrix deposition and interstitial fibrosis that accompany cardiac hypertrophy can contribute to the pathophysiology of heart failure. By inhibiting collagen I production, IFN-γ may reduce interstitial fibrosis in the setting of heart failure.

TABLE 1

Body Weight and Organ Weight in Rats Treated with Flup and/or IFN

|  | Vehicle | Flup | Flup + IFN | IFN |
|---|---|---|---|---|
| BWO (g) | 292.4 ± 1.7 | 292.3 ± 2.2 | 292.8 ± 2.1 | 292.5 ± 3.2 |
| BW (g) | 391.6 ± 6.3 | 381.1 ± 4.4 | 377.6 ± 4.5 | 380.8 ± 6.1 |
| ΔBW (g) | 99.2 ± 5.5 | 91.9 ± 4.0 | 84.8 ± 3.9 | 88.3 ± 5.0 |
| HW (g) | .966 ± .022 | 1.000 ± .018 | .9279 ± .016# | .956 ± .029 |
| VW (g) | .922 ± .022 | .957 ± .017 | .889 ± .015# | .914 ± .029 |
| LVW (g) | .706 ± .018 | .740 ± .013 | .678 ± .011## | .696 ± .023 |
| KW (g) | 1.440 ± .035 | 1.397 ± .038 | 1.377 ± .031 | 1.327 ± .035* |
| KW/BW (g/kg) | 3.678 ± .075 | 3.632 ± .076 | 3.648 ± .070 | 3.483 ± .069 |
| SW (g) | .799 ± .050 | .880 ± .048 | 1.009 ± .042* | .924 ± .068 |
| SW/BW (g/kg) | 2.065 ± .149 | 2.309 ± .130 | 2.676 ± .082** | 2.415 ± .149 |

Data expressed as mean ± SEM, and animal numbers are 14, 14, 14, and 9 in the Vehicle, Flup, Flup + IFN, and IFN group, respectively. Vehicle, saline; Flup, fluprostenol; IFN, interferon γ, BWO, basal levels of body weight; BW, body weight post treatment; ΔBW, BW-BWO; HW, heart weight; VW, ventricular weight; LVW, left ventricular weight; KW, kidney weight; SW, spleen weight.
*$p < 0.05$, **$P < 0.01$, compared to the Vehicle group, #$p < 0.05$, ##$p < 0.01$, compared to the Flup group.

TABLE 2

Body Weight, Organ Weight, and HR in Rats with Pressure Overload

|  | Sham | PO + vehicle | PO + IFN |
|---|---|---|---|
| BWO (g) | 278.8 ± 1.9 | 279.4 ± 1.3 | 279.0 ± 1.3 |
| BW (g) | 367.9 ± 6.8 | 347.5 ± 5.7* | 355.5 ± 5.2 |
| ΔBW (g) | 89.1 ± 5.8 | 68.1 ± 5.6* | 76.5 ± 4.7 |
| AW (g) | .038 ± .002 | .056 ± .002** | .046 ± .003*## |
| AW/BW (g/kg) | .104 ± .004 | .162 ± .006** | .129 ± .007*## |
| KW (g) | 1.438 ± .051 | 1.334 ± .033 | 1.349 ± .071 |
| KWBW (g/kg) | 3.894 ± .078 | 3.841 ± .070 | 3.776 ± .071 |
| LW (g) | 13.84 ± .55 | 12.53 ± .36 | 13.96 ± .47# |
| LW/BW (g/kg) | 37.46 ± .96 | 36.01 ± .71 | 38.94 ± .92# |
| SW (g) | .724 ± .030 | .839 ± .026* | 1.170 ± .053**## |
| SW/BW (g/kg) | 1.959 ± .051 | 2.418 ± .069** | 3.261 ± .121**## |
| HR (bpm) | 371 ± 12 | 415 ± 12* | 418 ± 19* |

Data expressed as mean ± SEM. Animal numbers are 16, 22, and 21 in the Sham, PO + vehicle, and PO + IFN group, respectively, for all parameters except HR for which animal number are 7, 8, and 7, respectively. PO, pressure overload; IFN, interferon γ; BWO, basal levels of body weight; BW, body weight post treatment; ΔBW, BW-BWO; AW, atrial weight; KW, kidney weight; LW, liver weight; SW, spleen weight; HR, heart rate.
*$p < 0.05$, **$P < 0.01$, compared to the sham group. #$p < 0.05$, ##$p < 0.01$, compared to the PO + vehicle group.

TABLE 3

Effect of IFN on Gene Expression

| Treatment | SHAM + Vehicle | PO + Vehicle | PO + IFN |
|---|---|---|---|
| ANF | 0.98 ± 0.37 | 5.29 ± 1.21† | 3.61 ± 1.32 |
| βMHC | 0.89 ± 0.24 | 1.91 ± 0.15† | 1.71 ± 0.14† |
| SKA | 0.95 ± 0.13 | 3.35 ± 0.46† | 2.47 ± 0.51† |
| SMA | 0.71 ± 0.06 | 0.89 ± 0.04† | 0.77 ± 0.06 |
| COLI | 0.55 ± 0.05 | 0.91 ± 0.09† | 0.77 ± 0.10 |
| COLIII | 0.44 ± 0.05 | 0.66 ± 0.08† | 0.72 ± 0.09† |
| FIB | 0.66 ± 0.17 | 1.03 ± 0.11† | 0.97 ± 012 |

PO indicates pressure overload; IFN, interferon-gamma; ANF, atrial natriuretic factor; βMHC, β-myosin heavy chain; SKA, α-skeletal actin; SMA, α-smooth muscle actin; COLI, collagen I; COLIII, collagen III; FIB, fibronectin.
Expression levels are calculated as ratios to glyceraldehyde-3-phosphate dehydrogenase. n = 6 per group Values are mean ± SEM. †P <0.05 vs sham + vehicle group. †

What is claimed is:

1. A method of treating cardiac hypertrophy comprising administering to a patient diagnosed with pressure overload induced cardiac hypertrophy a therapeutically effective amount of interferon gamma (IFN-γ).

2. The method of claim 1 wherein said patient is human.

3. The method of claim 2 wherein said IFN-γ is rhIFN-γ-1b.

4. The method of claim 2 wherein said IFN-γ is administered in combination with at least one further therapeutic agent used for the treatment of cardiac hypertrophy or a heart disease resulting in cardiac hypertrophy.

5. The method of claim 4 wherein said further therapeutic agent is selected from the group consisting of β-adrenergic-blocking agents, verapamil, difedipine, and diltiazem.

6. The method of claim 5 wherein said β-adrenergic-blocking agent is carvedilol, propranolol, metaprolol, timolol, exprenolol or tertatolol.

7. The method of claim 4 wherein said IFN-γ is administered in combination with an antihypertensive drug.

8. The method of claim 4 wherein said IFN-γ is administered with an ACE-inhibitor.

9. The method of claim 4 wherein said IFN-γ is administered with an endothelin receptor antagonist.

10. The method of claim 4 wherein said IFN-γ is administered following the administration of a thrombolytic agent.

11. The method of claim 10 wherein said thrombolytic agent is recombinant human tissue plasminogen activator (rht-PA).

12. The method of claim 4 wherein said IFN-γ is administered following primary angioplasty for the treatment of acute myocardial infarction.

* * * * *